United States Patent [19]

Van Daele et al.

[11] Patent Number: 5,185,335
[45] Date of Patent: Feb. 9, 1993

[54] N-(4-PIPERODINYL)(DIHYDROBENZOFURAN OR DIHYDRO-2H-BENZOPYRAN) CARBOXAMIDE DERIVATIVES

[75] Inventors: Georges H. P. Van Daele, Turnhout; Jean-Paul R. M. A. Bosmans, Kortrijk-Marke; Michel A. J. De Cleyn, Merksplas, all of Belgium

[73] Assignee: Janssen Pharmaceutica N.V., Beerse, Belgium

[21] Appl. No.: 650,328

[22] Filed: Feb. 4, 1991

[30] Foreign Application Priority Data

Mar. 6, 1990 [GB] United Kingdom ............... 9005014

[51] Int. Cl.$^5$ ............... A61K 31/53; A61K 31/54; A61K 43/58; A61K 43/60; A61K 31/495; A61K 31/47; A61K 31/445; C07D 513/00; C07D 487/00; C07D 403/00; C07D 241/36; C07D 405/00; C07D 215/00; C07D 490/00; C07D 401/00; C07D 217/00

[52] U.S. Cl. ............... 514/243; 514/226.5; 514/248; 514/249; 514/253; 514/258; 514/259; 514/307; 514/309; 514/310; 514/312; 514/313; 514/314; 514/315; 514/318; 514/320; 514/321; 514/322; 514/323; 514/324; 514/316; 544/180; 544/220; 544/235; 544/237; 544/238; 544/278; 544/282; 544/285; 544/48; 544/183; 544/236; 544/264; 544/296; 544/333; 544/353; 544/405; 546/139; 546/143; 546/144; 546/145; 546/146; 546/147; 546/148; 546/149; 546/152; 546/159; 546/118; 546/175; 546/187; 546/190; 546/193; 546/194; 546/196; 546/197; 546/199; 546/201; 546/214

[58] Field of Search ............... 544/180, 220, 235, 237, 544/238, 278, 282, 283, 285, 405, 333, 353; 514/243, 248, 253, 258, 259, 252, 256, 307, 309, 226.5, 249, 310, 312–314, 315, 318, 320–324, 316; 546/139, 143–145, 146–149, 152, 159, 175, 214, 190, 193, 194, 196, 199, 201, 197

[56] References Cited

U.S. PATENT DOCUMENTS

| | | | |
|---|---|---|---|
| 4,186,135 | 1/1980 | Thominet et al. | 260/326.34 |
| 4,434,170 | 2/1984 | Dostert et al. | 424/265 |
| 4,525,356 | 6/1985 | Itho et al. | 546/196 |
| 4,772,459 | 9/1988 | Sun et al. | 546/209 |
| 4,906,643 | 3/1990 | Van Daele et al. | 514/318 |
| 4,962,115 | 10/1990 | Van Daele | 514/326 |
| 4,975,439 | 12/1990 | Van Daele et al. | 514/316 |
| 5,006,570 | 4/1991 | Franceschini et al. | 514/422 |

FOREIGN PATENT DOCUMENTS

| | | |
|---|---|---|
| 0068700 | 1/1983 | European Pat. Off. |
| 0069481 | 1/1983 | European Pat. Off. |
| 0094742 | 11/1983 | European Pat. Off. |
| 0124783 | 11/1984 | European Pat. Off. |
| 0147044 | 7/1985 | European Pat. Off. |
| 0213775 | 3/1987 | European Pat. Off. |
| 0230718 | 8/1987 | European Pat. Off. |
| 0234872 | 9/1987 | European Pat. Off. |
| 0307172 | 3/1989 | European Pat. Off. |
| 0339950 | 11/1989 | European Pat. Off. |
| 0389037 | 9/1990 | European Pat. Off. |
| 2396757 | 2/1979 | France |
| WO-84/03281 | 8/1984 | PCT Int'l Appl. |
| WO-88/01866 | 3/1988 | PCT Int'l Appl. |
| 2160871 | 1/1986 | United Kingdom |
| 2207673A | 2/1989 | United Kingdom |

*Primary Examiner*—Cecilia Tsang
*Attorney, Agent, or Firm*—Charles J. Metz

[57] ABSTRACT

Piperidine derivatives of formula

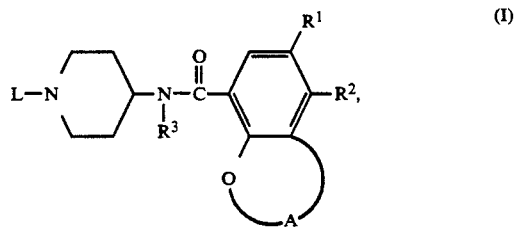

wherein A is a radical of formula

| | |
|---|---|
| $-CH_2-CH_2-$, | (a-1) |
| $-CH_2-CH_2-CH_2-$, or | (a-2) |
| $-CH_2-CH_2-CH_2-CH_2-$, | (a-3) | wherein one or two hydrogen atoms in said radicals (a-1) to (a-3) may be replaced by a $C_{1-6}$alkyl radical; $R^1$ is hydrogen or halo; $R^2$ is hydrogen, amino, mono or di($C_{1-6}$alkyl)amino or $C_{1-6}$alkylcarbonylamino; $R^3$ is hydrogen or $C_{1-6}$alkyl; L is $C_{3-6}$cycloalkyl, $C_{5-6}$cycloalkanone, $C_{3-6}$alkenyl optionally substituted with aryl, or L is a radical of formula

| | |
|---|---|
| $-Alk-R^4$, | (b-1) |
| $-Alk-X-R^5$, | (b-2) |
| $-Alk-Y-C(=O)-R^7$, or | (b-3) |
| $-Alk-Y-C(=O)-NR^9R^{10}$, | (b-4) | the N-oxide forms, addition salts and stereochemically isomeric forms thereof, said compounds having gastrointestinal motility stimulating properties. Pharmaceutical compositions containing these compounds as active ingredient, and a method of preparing said compounds and pharmaceutical compositions.

13 Claims, No Drawings

N-(4-PIPERODINYL)(DIHYDROBENZOFURAN OR DIHYDRO-2H-BENZOPYRAN) CARBOXAMIDE DERIVATIVES

BACKGROUND OF THE INVENTION

A number of substituted (3-hydroxy-4-piperidinyl)-benzamide derivatives have been described as stimulators of the motility of the gastrointestinal system in EP-A-0,076,530; EP-A-0,299,566 and EP-A-0,309,043.

In EP-A-0,307,172; EP-A-0,124,783; DE-3,702,005; EP-A-0,147,044; EP-A-0,234,872 and U.S. Pat. No. 4,772,459 there are described benzofuran, benzopyran or benzoxepin carboxamide derivatives being substituted on the nitrogen with an alkylamino group or with a mono- or bicyclic hetero ring optionally through an alkyl chain. These compounds are taught to be antiemetic, anti-psychotic or neuroleptic agents.

WO-A-84 03 281 describes N-azabicycloalkylbenzamides and -anilides useful as dopamine antagonists, antihypertensives and analgesic potentiators.

WO-A-88 01 866 describes N-heterocyclylbenzoheterocyclic amides useful as antiemetic agents especially for administration with cancer chemotherapeutic agents.

The N-(4-piperidinyl)(dihydrobenzofuran or dihydro-2H-benzopyran)carboxamide derivatives of the present invention differ therefrom structurally and pharmacologically by their favourable gastrointestinal motility stimulating properties.

DESCRIPTION OF THE INVENTION

The present invention is concerned with novel benzamide derivatives having the formula

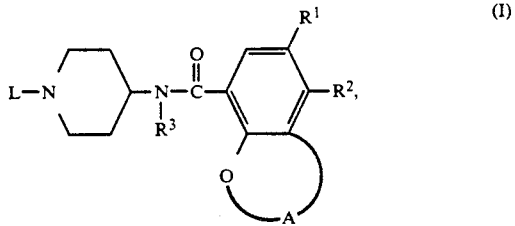

the N-oxide forms, the salts and the stereochemically isomeric forms thereof, wherein:

A is a radical of formula

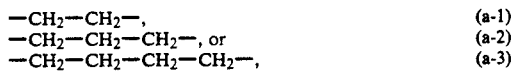

wherein one or two hydrogen atoms in said radicals (a-1) to (a-3) may be replaced by a $C_{1-6}$alkyl radical;

$R^1$ is hydrogen or halo;

$R^2$ is hydrogen, amino, mono or di($C_{1-6}$alkyl)amino or $C_{1-6}$alkylcarbonylamino;

$R^3$ is hydrogen or $C_{1-6}$alkyl;

L is $C_{3-6}$cycloalkyl, $C_{5-6}$cycloalkanone, $C_{3-6}$alkenyl optionally substituted with aryl, or L is a radical of formula

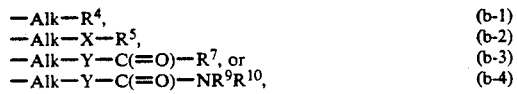

wherein each Alk is $C_{1-6}$alkanediyl; and $R^4$ is hydrogen, cyano, $C_{1-6}$alkylsulfonylamino, $C_{3-6}$cycloalkyl, $C_{5-6}$cycloalkanone, aryl, di(aryl)methyl or Het;

$R^5$ is hydrogen, $C_{1-6}$alkyl, hydroxy$C_{1-6}$alkyl, $C_{3-6}$cycloalkyl, aryl or Het;

X is O, S, $SO_2$ or $NR^6$; said $R^6$ being hydrogen, $C_{1-6}$alkyl or aryl;

$R^7$ is hydrogen, $C_{1-6}$alkyl, $C_{3-6}$cycloalkyl, aryl, aryl$C_{1-6}$alkyl, di(aryl)methyl, $C_{1-6}$alkyloxy or hydroxy;

Y is $NR^8$ or a direct bond; said $R^8$ being hydrogen, $C_{1-6}$alkyl or aryl;

$R^9$ and $R^{10}$ each independently are hydrogen, $C_{1-6}$alkyl, $C_{3-6}$cycloalkyl, aryl or aryl$C_{1-6}$alkyl, or $R^9$ and $R^{10}$ combined with the nitrogen atom bearing $R^9$ and $R^{10}$ may form a pyrrolidinyl or piperidinyl ring both being optionally substituted with $C_{1-6}$alkyl, amino or mono or di($C_{1-6}$alkyl)amino, or said $R^9$ and $R^{10}$ combined with the nitrogen bearing $R^9$ and $R^{10}$ may form a piperazinyl or 4-morpholinyl radical both being optionally substituted with $C_{1-6}$alkyl;

each aryl being unsubstituted phenyl or phenyl substituted with 1,2 or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino or aminocarbonyl; and each Het being a five- or six-membered heterocyclic ring containing 1,2,3 or 4 heteroatoms selected from oxygen, sulfur and nitrogen, provided that no more than 2 oxygen and/or sulfur atoms are present, said five- or six-membered ring being optionally condensed with a five- or six-membered carbocyclic or heterocyclic ring also containing 1,2,3 or 4 heteroatoms selected from oxygen, sulfur and nitrogen, provided that the latter ring does not contain more than 2 oxygen and/or sulfur atoms and that the total number of heteroatoms in the bicyclic ring system is less than 6; when Het is a monocyclic ring system it may optionally be substituted with up to 4 substituents; when Het is a bicyclic ringsystem it may optionally be substituted with up to 6 substituents; said substituents being selected from the group consisting of halo, hydroxy, cyano, trifluoromethyl, $C_{1-6}$alkyl, aryl$C_{1-6}$alkyl, aryl, $C_{1-6}$alkyloxy, $C_{1-6}$alkyloxy$C_{1-6}$alkyl, hydroxy$C_{1-6}$alkyl, $C_{1-6}$alkylthio, mercapto, nitro, amino, mono and di($C_{1-6}$alkyl)amino, aryl$C_{1-6}$alkylamino, aminocarbonyl, mono and di($C_{1-6}$alkyl)aminocarbonyl, $C_{1-6}$alkyloxycarbonyl, aryl$C_{1-6}$alkyloxycarbonyl, a bivalent radical =O and =S; provided that when $R^5$ is Het, Het is connected to X on a carbon atom.

As used in the foregoing definitions halo is generic to fluoro, chloro, bromo and iodo; $C_{1-6}$alkyl defines straight and branched chain saturated hydrocarbon radicals having from 1 to 6 carbon atoms such as, for example, methyl, ethyl, propyl, butyl, hexyl, 1-methylethyl, 2-methylpropyl and the like; $C_{3-6}$cycloalkyl defines cyclopropyl, cyclobutyl, cyclopentyl and cyclohexyl; $C_{5-6}$cycloalkanone defines cyclopentanone and cyclohexanone; $C_{3-6}$alkenyl defines straight and branched chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and when a $C_{3-6}$alkenyl is substituted on a heteroatom, then the carbon atom of said $C_{3-6}$alkenyl connected to said heteroatom preferably is saturated; $C_{1-6}$alkanediyl defines bivalent straight or branched chain hydrocarbon radicals containing from 1 to 6 carbon atoms such as, for example, 1,2-ethanediyl, 1,3-propanediyl, 1,4-butanediyl, 1,5-pentanediyl, 1,6-hexanediyl and the branched isomers thereof.

The salts as mentioned hereinabove are meant to comprise the therapeutically active non-toxic addition salt forms which the compounds of formula (I) are able to form. The latter can conveniently be obtained by treating the base form with such appropriate acids as inorganic acids, for example, hydrohalic acids, e.g. hydrochloric, hydrobromic and the like, sulfuric acid, nitric acid, phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted into their therapeutically active non-toxic metal or amine salt forms by treatment with appropriate organic or inorganic bases.

The term addition salt also comprises the hydrates and solvent addition forms which the compounds of formula (I) are able to form. Examples of such forms are e.g. hydrates, alcoholates and the like.

As defined hereinabove, $R^7$ may be hydroxy and in that instance Y in radical (b-3) in particular is a direct bond.

The N-oxides of the compounds of formula (I) are meant to comprise those compounds of formula (I) wherein one or several nitrogen atoms are oxidated to the N-oxide form, in particularly those N-oxides wherein the piperidine-nitrogen is N-oxidated.

In the compounds of formula (I) wherein $R^4$ and $R^5$ is Het, said Het may be partly or completely saturated, or unsaturated. The compounds of formula (I) wherein Het is partly saturated or unsaturated and is substituted with hydroxy, mercapto or amino, may also exist in their tautomeric forms. Such forms although not explicitly indicated hereinabove, are intended to be included within the scope of the invention.

In particular, Het may be:

i) an optionally substituted five- or six-membered heterocyclic ring containing 1, 2, 3 or 4 heteroatoms selected from oxygen, sulfur and nitrogen, provided that no more than 2 oxygen and/or sulfur atoms are present; or ii) an optionally substituted five- or six-membered heterocyclic ring containing 1, 2 or 3 heteroatoms selected from oxygen, sulfur and nitrogen, being fused with an optionally substituted five- or six-membered ring through 2 carbon atoms or 1 carbon and 1 nitrogen atom, containing in the remainder of the fused ring only carbon atoms; or iii) an optionally substituted five- or six-membered heterocyclic ring containing 1,2 or 3 heteroatoms selected from oxygen, sulfur and nitrogen, being fused with an optionally substituted five- or six-membered heterocyclic ring through 2 carbon atoms or 1 carbon and 1 nitrogen atom, containing in the remainder of the fused ring 1 or 2 heteroatoms selected from oxygen, sulfur and nitrogen;

wherein Het being a monocyclic ring system may be optionally substituted with up to 4 substituents; and wherein Het being a bicyclic ring system may be optionally substituted with up to 6 substituents, said substituents being the same as defined hereinabove.

A more particular subgroup of Het comprises cyclic ether or thioether ring systems containing one or two oxygen and/or sulfur atoms, provided that when two oxygen and/or sulfur atoms are present, they are in non-adjacent positions in the ring. Said cyclic ether or thioether ring systems are optionally condensed with a five- or six-membered carbocyclic ring. These cyclic ether or thioether ring systems may also be substituted with one or more $C_{1-6}$alkyl, $C_{1-6}$alkyloxy, $C_{1-6}$alkyloxy$C_{1-6}$alkyl or hydroxy$C_{1-6}$alkyl substituents. This subgroup of Het radicals will be represented by the symbol $Het^1$.

Typical cyclic ethers and thioethers which are covered by $R^4$ being Het in the compounds of the present invention can be represented by the following formulae:

(c-1)

(c-2)

(c-3)

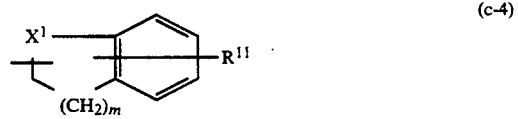
(c-4)

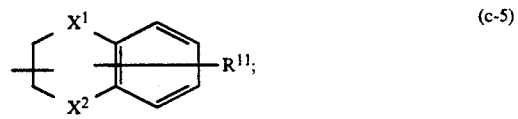
(c-5)

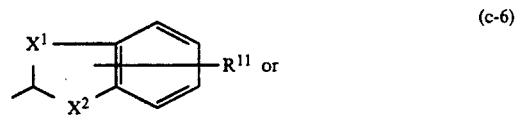
(c-6)

(c-7)

wherein
each $X^1$ and $X^2$ independently are O or S;
m is 1 or 2;
each $R^{11}$ is hydrogen, $C_{1-4}$alkyl, $C_{1-4}$alkyloxy$C_{1-4}$alkyl or hydroxy-$C_{1-4}$alkyl and
$R^{12}$ is hydrogen, halo or $C_{1-4}$alkyl.

Further particular cyclic ethers are selected from the group consisting of 1,3-dioxolanyl optionally substituted with $C_{1-4}$alkyl; 1,3-dioxanyl optionally substituted with $C_{1-4}$alkyl; tetrahydrofuranyl optionally substituted with $C_{1-4}$alkyl; tetrahydropyranyl optionally substituted with $C_{1-4}$alkyl; 2,3-dihydro-1,4-benzodioxinyl; 2,3-dihydrobenzofuran and 3,4-dihydro-1(2H)-benzopyranyl, with tetrahydrofuranyl being preferred.

Another more particular subgroup of Het comprises heterocyclic ring systems which are selected from the group consisting of pyrrolidinyl; piperidinyl; pyridinyl which is optionally substituted with one or two substituents each independently selected from halo, hydroxy, cyano, $C_{1-6}$alkyl, trifluoromethyl, $C_{1-6}$alkyloxy, aminocarbonyl, mono and di($C_{1-6}$alkyl)aminocarbonyl, amino, mono and di($C_{1-6}$alkyl)amino and $C_{1-6}$alkyloxycarbonyl; pyrimidinyl which is optionally substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl which is optionally substituted with $C_{1-6}$alkyl or halo; pyrazinyl which is optionally substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl; pyrrolyl which is optionally substituted with $C_{1-6}$alkyl; pyrazolyl which is optionally substituted with $C_{1-6}$alkyl; imidazolyl which is optionally substituted with $C_{1-6}$alkyl; triazolyl which is optionally substituted with $C_{1-6}$alkyl; quinolinyl optionally substituted with up to two substituents each independently selected from halo, hydroxy, cyano, $C_{1-6}$alkyl, $C_{1-6}$alkyloxy, amino, mono and di($C_{1-6}$alkyl)amino and trifluoromethyl; isoquinolinyl optionally substituted with up to two substituents each independently selected from halo, hydroxy, cyano, $C_{1-6}$alkyl, $C_{1-6}$alkyloxy, amino, mono and di($C_{1-6}$alkyl)amino and trifluoromethyl; quinoxalinyl optionally substituted with up to two substituents each independently selected from $C_{1-6}$alkyl, hydroxy, halo, cyano and $C_{1-6}$alkyloxy; quinazolinyl optionally substituted with $C_{1-6}$alkyl; benzimidazolyl optionally substituted with $C_{1-6}$alkyl; indolyl optionally substituted with $C_{1-6}$alkyl; 5,6,7,8-tetrahydroquinolinyl optionally substituted with up to two substituents each independently selected from halo, hydroxy, cyano, $C_{1-6}$alkyl, $C_{1-6}$alkyloxy, amino, mono- and di($C_{1-6}$alkyl)amino and trifluoromethyl; 5,6,7,8-tetrahydroquinoxalinyl optionally substituted with up to two substituents each independently selected from $C_{1-6}$alkyl, hydroxy, halo, cyano and $C_{1-6}$alkyloxy; thiazolyl optionally substituted with $C_{1-6}$alkyl; oxazolyl optionally substituted with $C_{1-6}$alkyl; benzoxazolyl optionally substituted with $C_{1-6}$alkyl; benzothiazolyl optionally substituted with $C_{1-6}$alkyl. This subgroup of Het radicals will be represented by the symbol $Het^2$.

Further particular heterocyclic ring systems within this subgroup are for example, piperidinyl, pyridinyl optionally substituted with up to two substituents selected from $C_{1-4}$alkyl, cyano, halo and trifluoromethyl; pyrazinyl optionally substituted with cyano, halo, $C_{1-4}$alkyloxycarbonyl and $C_{1-4}$alkyl; and pyridazinyl optionally substituted with halo.

Another more particular subgroup of Het comprises optionally substituted five- or six-membered cyclic amides containing one, two or three nitrogen atoms, said five or six-membered heterocyclic ring being optionally condensed with a five- or six-membered carbocyclic or heterocyclic ring containing one or two nitrogen atoms or one sulfur or oxygen atom. This subgroup of Het will be represented hereinafter by the symbol $Het^3$.

Typical monocyclic amides covered by $R^4$ and $R^5$ being Het in the compounds of the present invention, can be represented by the following formulae:

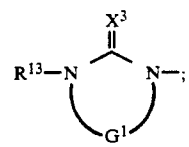
(d-1)

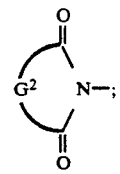
(d-2)

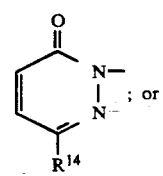
(d-3)

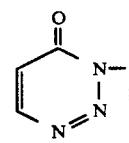
(d-4)

where
$X^3$ is O or S;
$R^{13}$ is hydrogen, $C_{1-6}$alkyl or aryl$C_{1-6}$alkyl;
$R^{14}$ is hydrogen, halo, $C_{1-6}$alkyl or aryl;
$G^1$ is —$CH_2$—$CH_2$—, —CH=CH—, —N=N—, —C(=O)—$CH_2$— or —$CH_2$—$CH_2$—$CH_2$—, wherein one or two hydrogen atoms each independently may be replaced by $C_{1-6}$alkyl; and
$G^2$ is —$CH_2$—$CH_2$—, —$CH_2$—N($R^{13}$)— or —$CH_2$—$CH_2$—$CH_2$—, wherein one or two hydrogen atoms each independently may be replaced by $C_{1-6}$alkyl.

Typical bicyclic amides covered by the definition of $R^4$ and $R^5$ being Het, can be represented by the following formulae:

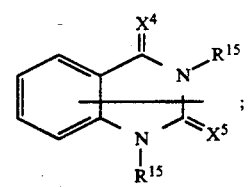
(d-5)

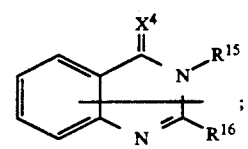
(d-6)

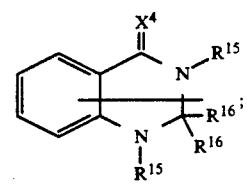
(d-7)

-continued

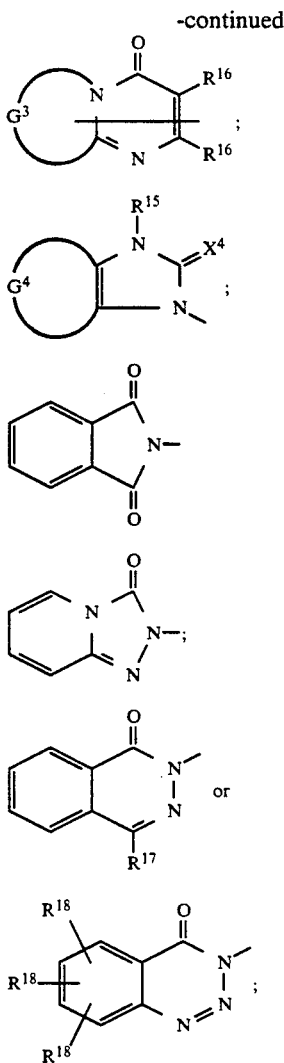

(d-8)

(d-9)

(d-10)

(d-11)

(d-12)

(d-13)

wherein
$X^4$ and $X^5$ each independently are O or S;

each $R^{15}$ independently is hydrogen, $C_{1-6}$alkyl or aryl$C_{1-6}$alkyl;

each $R^{16}$ independently is hydrogen, halo, $C_{1-6}$alkyl or $C_{1-6}$alkyloxy; $R^{17}$ is hydrogen, halo, $C_{1-6}$alkyl or aryl; and each $R^{18}$ independently is hydrogen, $C_{1-6}$alkyloxy or $C_{1-6}$alkyl wherein the radicals (d-5), (d-6), (d-7) and (d-8) may be connected to respectively Alk or X by replacing either a hydrogen or a radical $R^{15}$ and $R^{16}$ by a free bond;

$G^3$ is —CH=CH—CH=CH—, —(CH$_2$)$_4$—, —S—(CH$_2$)$_2$—, —S—(CH$_2$)$_3$—, —S—CH=CH—, —CH=CH—O—, —NH—(CH$_2$)$_2$—, —NH—(CH$_2$)$_3$—, —NH—CH=CH—, —NH—N=CH—CH$_2$—, —NH—CH=N— or —NH—N=CH—;

$G^4$ is —CH=CH—CH=CH—, —CH=CCl—CH=CH—, —CCl=CH—CH=CH—, —N=CH—CH=CH—, —CH=N—CH=CH—, —CH=CH—N=CH—, —CH=CH—CH=N—, —N=CH—N=CH— or —CH=N—CH=N—.

Further particular heterocyclic ring systems within this subgroup are selected from the group consisting of 2,3-dihydro-2-oxo-1H-benzimidazolyl optionally substituted with $C_{1-6}$alkyl; 2-oxo-1-imidazolidinyl optionally substituted with $C_{1-4}$alkyl; 2,5-dioxo-1-imidazolidinyl optionally substituted with $C_{1-4}$alkyl; 3,4-dihydro-4-oxo-1,2,3-benzotriazin-3-yl optionally substituted with 1,2 or 3 $C_{1-4}$alkyloxy groups; 1-oxo-2(1H)-phthalazinyl; 2,3-dihydro-5-oxo-5H-thiazolo[3,2-a]pyrimidin-6-yl optionally substituted with $C_{1-4}$alkyl; 5-oxo-5H-thiazolo[3,2-a]pyrimidin-6-yl optionally substituted with $C_{1-4}$alkyl; 1,6-dihydro-6-oxo-1-pyridazinyl optionally substituted with $C_{1-4}$alkyl or halo; and 1,2,3,4-tetrahydro-2,4-dioxo-3-quinazolinyl.

Interesting compounds within the invention are those compounds of formula (I) wherein $R^1$ is hydrogen or halo; and/or $R^2$ is hydrogen, amino or $C_{1-6}$alkylamino; and/or $R^3$ is hydrogen.

Other interesting compounds within the invention are those compounds of formula (I) wherein $R^1$ is hydrogen or halo; and/or $R^2$ is hydrogen, amino or $C_{1-6}$alkylamino; and/or $R^3$ is $C_{1-4}$alkyl.

More interesting compounds are those interesting compounds wherein

L is $C_{3-6}$cycloalkyl or $C_{3-6}$alkenyl optionally substituted with aryl; or L is a radical of formula (b-1) wherein $R^4$ is hydrogen, cyano, $C_{3-6}$cycloalkyl, $C_{5-6}$cycloalkanone, aryl, di(aryl)methyl or Het; or L is a radical of formula (b-2) wherein X is O, S or NH and $R^5$ is hydrogen, $C_{1-4}$alkyl, $C_{3-6}$cycloalkyl, aryl or Het; or L is a radical of formula (b-3) wherein Y is $NR^8$ or a direct bond, $R^8$ is hydrogen or aryl and $R^7$ is hydrogen, $C_{1-4}$alkyl, aryl, $C_{1-4}$alkyloxy or hydroxy; or L is a radical of formula (b-4) wherein Y is NH or a direct bond and $R^9$ and $R^{10}$ each independently are hydrogen or $C_{1-4}$alkyl, or $R^9$ and $R^{10}$ combined with the nitrogen bearing said $R^9$ and $R^{10}$ may form a pyrrolidinyl or piperidinyl radical.

Most interesting compounds are those more interesting compounds wherein A is a radical of formula (a-1) or (a-2) wherein the carbon atom adjacent to the oxygen atom is optionally substituted with one or two $C_{1-4}$alkyl substituents.

Preferred compounds are those most interesting compounds wherein

L is $C_{5-6}$cycloalkyl or $C_{3-6}$alkenyl optionally substituted with aryl; or L is a radical of formula (b-1) wherein Alk is $C_{1-4}$alkanediyl and $R^4$ is cyano, $C_{3-6}$cycloalkyl, diarylmethyl or Het; or L is a radical of formula (b-2) wherein Alk is $C_{1-4}$alkanediyl, X is O or NH and $R^5$ is hydrogen, $C_{1-4}$alkyl, $C_{3-6}$cycloalkyl, aryl or Het; or L is a radical of formula (b-3) wherein Alk is $C_{1-4}$alkanediyl, Y is NH or a direct bond and $R^7$ is $C_{1-4}$alkyl, aryl, $C_{1-4}$alkyloxy or hydroxy.

More preferred compounds are those preferred compounds wherein

Het is pyrrolidinyl; piperidinyl; pyridinyl optionally substituted with $C_{1-6}$alkyl or cyano; pyrazinyl optionally substituted with $C_{1-6}$alkyl; benzimidazolyl optionally substituted with $C_{1-6}$alkyl; or indolyl optionally substituted with $C_{1-6}$alkyl; or Het is a radical or formula (c-1), (c-2) or (c-4); or Het is a radical of formula (d-1), (d-3), (d-5), (d-8), (d-9), (d-12) or (d-13).

Particular preferred compounds are those more preferred compounds wherein Het is tetrahydrofuranyl optionally substituted with $C_{1-4}$alkyl; 1,3-dioxalanyl optionally substituted with $C_{1-4}$alkyl; 3,4-dihydro- 1(2H)-benzopyranyl; pyrrolidinyl; piperidinyl; pyridinyl optionally substituted with cyano; pyrazinyl optionally substituted with $C_{1-4}$alkyl; benzimidazolyl; indolyl; 2,3-dihydro-2-oxo-1H-benzimidazolyl optionally substituted with $C_{1-4}$alkyl; 2-oxo-1-imidazolidinyl optionally substituted with $C_{1-4}$alkyl; 3,4-dihydro-4-oxo-1,2,3-benzotriazin-3-yl optionally substituted with three $C_{1-4}$alkyloxy groups; 1-oxo-2(1H)-phthalazinyl; 2,3-dihydro-5-oxo-5H-thiazolo-[3,2-a]pyrimidin-6-yl optionally substituted with $C_{1-4}$alkyl; 5-oxo-5H-thiazolo-[3,2-a]pyrimidin-6-yl optionally substituted with $C_{1-4}$alkyl; 1,6-dihydro-6-oxo-1-pyridazinyl optionally substituted with $C_{1-4}$alkyl or halo; and 1,2,3,4-tetrahydro-2,4-dioxo-3-quinazolinyl.

More particular preferred compounds are those preferred compounds wherein $R^1$ is hydrogen or chloro; and/or $R^2$ is hydrogen, amino or (1-methylethyl)amino; and/or $R^3$ is hydrogen; and/or L is a radical of formula (b-1) wherein $R^4$ is cyano, cyclopentyl, tetrahydrofuranyl, piperidinyl, 7-methyl-5-oxo-5H-thiazolo[3,2-a]pyrimidin-6-yl; 3-ethyl-2,3-dihydro-2oxo-1H-benzimidazolyl; 1,6-dihydro-3-methyl-6-oxo-1-pyridazinyl; or L is a radical of formula (b-2) wherein X is O or NH and $R^5$ is H or 4-fluorophenyl; or L is a radical of formula (b-3) wherein Y is NH or direct bond and $R^7$ is methyl, ethoxy or 3,4,5-trimethoxyphenyl.

Most preferred compounds are 5-amino-6-chloro-3,4-dihydro-N-[1[(tetrahydro-2-furanyl)methyl]-4-piperidinyl]-2H-1-benzopyran-8-carboxamide;

(−)-(R)-5-amino-6-chloro-3,4-dihydro-N-[1-[(tetrahydro-2-furanyl)methyl]-4-piperidinyl]-2H-1-benzopyran-8-carboxamide;

4-amino-5-chloro-2,3-dihydro-N-[1-[(tetrahydro-2-furanyl)methyl]-4-piperidinyl]-7-benzofurancarboxamide;

(−)-(R)-4-amino-5-chloro-2,3-dihydro-N-[1-[(tetrahydro-2-furanyl)methyl]-4-piperidinyl]-7-benzofurancarboxamide;

(+)-(S)-4-amino-5-chloro-2,3-dihydro-N-[1-[(tetrahydro-2-furanyl)methyl]-4-piperidinyl]-7-benzofurancarboxamide;

ethyl [2-[4-[[(5-amino-6-chloro-3,4-dihydro-2H-1-benzopyran-8-yl)carbonyl]amino]-1-piperidinyl]ethyl]-carbamate;

5-amino-6-chloro-N-[1-[4-(3-ethyl-2,3-dihydro-2-oxo-1H-benzimidazol-1-yl)butyl]-4-piperidinyl]-3,4-dihydro-2H-1-benzopyran-8-carboxamide;

ethyl 4-[[(5-amino-6-chloro-3,4-dihydro-2H-1-benzopyran-8-yl)carbonyl]amino]-1-piperidinebutanoate;

5-amino-6-chloro-3,4-dihydro-N-[1-(4-oxopentyl)-4-piperidinyl]-2H-1-benzopyran-8-carboxamide; and 4-amino-5-chloro-2,3-dihydro-2,2-dimethyl-N-[1-(4-oxopentyl)-4-piperidinyl]-7-benzofurancarboxamide, the stereoisomers and the pharmaceutically acceptable acid-addition salts thereof.

In order to simplify the structural representations of the compounds of formula (I) and of certain starting materials and intermediates thereof, the radical

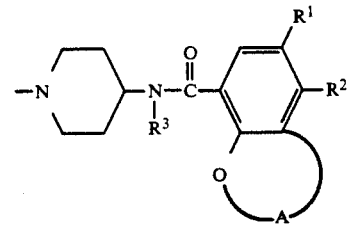

will hereafter be represented by the symbol D.

The compounds of formula (I) can be prepared by N-alkylating a piperidine of formula (II) with an intermediate of formula (III).

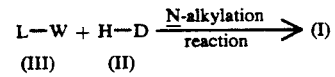

W as described in the reaction of (III) with (II) and in the following reaction schemes is an appropriate leaving group such as, for example, halo, preferably, chloro, bromo or iodo, or a sulfonyloxy group, e.g. methanesulfonyloxy, 4-methylbenzenesulfonyloxy and the like leaving groups.

The N-alkylation reaction of (II) with (III) is conveniently conducted in a reaction-inert solvent such as, for example, water; an aromatic hydrocarbon, e.g. benzene, methylbenzene, dimethylbenzene, chlorobenzene, methoxybenzene and the like; an alkanol, e.g. methanol, ethanol, 1-butanol and the like; a halogenated hydrocarbon, e.g. dichloromethane, trichloromethane and the like; an ester, e.g. ethyl acetate, γ-butyrolactone and the like; a ketone, e.g. 2-propanone, 4-methyl-2-pentanone and the like; an ether, e.g. 1,4-dioxane, 1,1'-oxybisethane, tetrahydrofuran and the like; a polar aprotic solvent, e.g. N,N-dimethylformamide, N,N-dimethylacetamide, dimethylsulfoxide, hexamethylphosphoric triamide, 1,3-dimethyl-3,4,5,6-tetrahydro-2(1H)-pyrimidinone, 1,3-dimethyl-2-imidazolidinone, 1,1,3,3-tetramethylurea, nitrobenzene, 1-methyl-2-pyrrolidinone and the like, or a mixture of such solvents.

The addition of an appropriate base such as, for example, an alkali or an earth alkaline metal carbonate, hydrogen carbonate, carboxylate, amide, oxide, hydroxide or alkoxide, e.g. sodium carbonate, sodium hydrogen carbonate, potassium carbonate, calcium oxide, sodium acetate, sodium amide, sodium hydroxide, sodium methoxide and the like or an organic base such as, for example, an amine, e.g. N,N-dimethyl-4-pyridinamine, N,N-diethylethanamine, N-(1-methylethyl)-2-propanamine, 1,4-diazabicyclo[2,2,2]octane, 4-ethylmorpholine and the like, may be utilized to pick up the acid which is liberated during the course of the reaction. In some instances the addition of a iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction. Additionally, it may be advantageous to conduct said N-alkylation under an inert atmosphere such as, for example, oxygen-free argon or nitrogen gas. Alternatively, said N-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

In this and the following preparations, the reaction products may be isolated from the reaction mixture and, if necessary, further purified according methodologies generally known in the art such as, for example, extraction, distillation, crystallization, trituration and chromatography.

The compounds of formula (I) can also be prepared by the amidation reaction of an amine of formula

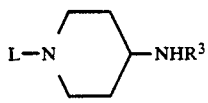

(IV)

with a carboxylic acid of formula

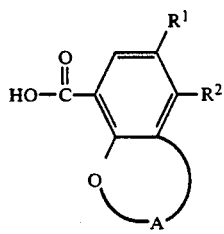

(V)

or a functional derivative thereof, such as a halide, a symmetrical or mixed anhydride or an ester, preferably an activated ester. Said functional derivative may be generated in situ, or if desired, be isolated and further purified before reacting it with the amine of formula (IV). Functional derivatives may be prepared following art-known procedures, for example, by reacting the carboxylic acid of formula (V) with thionyl chloride, phosphorous trichloride, phosphoryl chloride and the like, or by reacting the carboxylic acid of formula (V) with an acyl halide, e.g. acetyl chloride, ethyl carbonochloridate and the like. Or the intermediates (IV) and (V) may be coupled in the presence of a suitable reagent capable of forming amides, e.g. dicyclohexylcarbodiimide, 2-chloro-1-methylpyridinium iodide and the like.

Said amidation reactions may conveniently be carried out by stirring the reactants in a suitable reaction-inert solvent such as, for example, a halogenated hydrocarbon, e.g. dichloromethane, trichloromethane and the like, an aromatic hydrocarbon, e.g. methylbenzene and the like, an ether, e.g. 1,1'-oxybisethane, tetrahydrofuran and the like or a dipolar aprotic solvent, e.g. N,N-dimethylformamide, N,N-dimethylacetamide and the like. The addition of a suitable base may be appropriate, in particular a tertiary amine such as, N,N-diethylethanamine. The water, the alcohol or the acid which is liberated during the course of the reaction may be removed from the reaction mixture according to methodologies generally known in the art such as, for example, azeotropical distillation, complexation or salt formation. Further it may be expedient to protect amino or hydroxy groups during the course of the reaction to avoid undesired side reactions. Suitable protecting groups comprises readily removable groups such as, $C_{1-6}$alkylcarbonyl, $C_{1-4}$alkyloxycarbonyl, arylmethyl, tertiary butyl and the like protective groups.

The compounds of formula (I) can alternatively be prepared by the reductive N-alkylation reaction of an appropriate ketone or aldehyde of formula $L'=O$ (VI), said $L'=O$ being a compound of formula L-H wherein two geminal hydrogen atoms in the $C_{1-6}$alkanediyl or $C_{3-6}$cycloalkanediyl moiety are replaced by $=O$, with a piperidine of formula H-D (II).

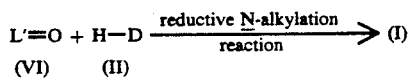

Said reductive N-alkylation reaction may conveniently be carried out by reducing a mixture of the reactants in a suitable reaction-inert solvent. In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethylacetate, γ-butyrolactone and the like; ethers, e.g. 1,4-dioxane, tetrahydrofuran, 1,1'-oxybisethane, 2-methoxyethanol and the like; dipolar aprotic solvents, e.g. N,N-dimethylformamide, dimethyl sulfoxide and the like; carboxylic acids, e.g. acetic acid, propanoic acid and the like; or a mixture of such solvents. The term "art-known reductive N-alkylation procedures" means that the reaction is carried out either with sodium cyanoborohydride, sodium borohydride, formic acid or a salt thereof, e.g. ammonium formate and the like reducing agents, or alternatively under hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g., thiophene, quinoline, sulphur and the like. In some instances it may also be advantageous to add an alkali metal salt to the reaction mixture such as, for example, potassium fluoride, potassium acetate and the like salts.

The compounds of formula (I) wherein L is a radical of formula (b-2) and $R^5$ is aryl or Het, said $R^5$ being represented by $R^{5-a}$, can alternatively be prepared according to one of the following alkylation procedures.

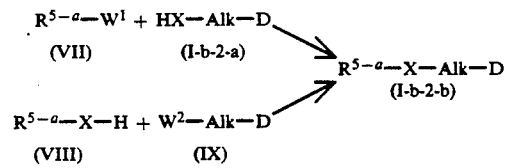

In (VII) and (IX) $W^1$ and $W^2$ are appropriate leaving groups such as, for example, halo, e.g. chloro or bromo, $C_{1-6}$alkyloxy or $C_{1-6}$alkylthio, e.g. methoxy or methylthio. $W^2$ can also be a sulfonyloxygroup or pyridinium group.

The alkylation reactions of (VII) with (I-b-2-a) and (VIII) with (IX) can be carried out according to art-known procedures, e.g. by stirring the reactants without a solvent or in an inert organic solvent such as, for example, an aromatic hydrocarbon, e.g. benzene, methylbenzene, dimethylbenzene, and the like, a lower alkanol, e.g. methanol, ethanol. 1-butanol and the like, a ketone, e.g. 2-propanone, 4-methyl-2-pentanone and the like, an ether, e.g. 1,4-dioxane, 1,1'-oxybisethane, tetrahydrofuran and the like, a polar aprotic solvent, e.g. N,N-dimethylformamide, N,N-dimethylacetamide, dimethylsulfoxide, nitrobenzene, 1-methyl-2-pyrrolidinone and the like or a mixture of two or more of such solvents. The addition of an appropriate base such as, for example, an alkali or an earth alkaline metal carbonate, hydrogen carbonate, hydroxide, alkoxide, hydride, amide or oxide, e.g. sodium carbonate, sodium hydrogen carbonate, potassium carbonate, sodium hydroxide, sodium methoxide, sodium hydride, sodium amide, calcium carbonate, calcium hydroxide, calcium oxide and the like or an organic base, such as, for example, a tertiary amine, e.g. N,N-diethylethanamine, N-(1-methylethyl)-2-propanamine, 4-ethylmorpholine and the like, may be utilized to pick up the acid which is liberated during the course of the reaction. In some instances the addition of a iodide salt, preferably an alkali metal iodide or a crown ether, e.g. 1,4,7,10,13,16-hexaoxacyclooctadecane and the like, may be approriate.

The compounds of formula (I) wherein L is a radical of formula (b-4), said compounds being represented by (I-b-4), can also be prepared by reacting a piperdine of formula (X) with an amine of formula (XI).

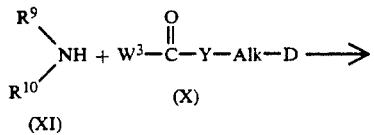

(XI)           (X)

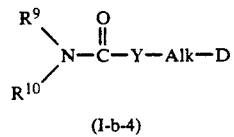

(I-b-4)

In (XI) $R^9$ and $R^{10}$ have the same meanings as described hereinbefore. $W^3$ is an appropriate leaving group such as, for example, halo, e.g. chloro or bromo; hydroxy; $C_{1-6}$alkyloxy or $C_{1-6}$alkylthio, e.g. methoxy or methylthio.

The compounds of formula (I) wherein L is a radical of formula (b-4) and Y is $NR^8$, said compounds being represented by (I-b-4-a), can also be prepared by reacting an amide of formula (XII) with an amine of formula (XIII). $W^4$ is an appropriate leaving group such as, for example, hydroxy; $C_{1-6}$alkyloxy, e.g. methoxy.

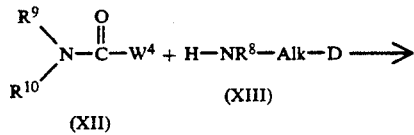

(XII)           (XIII)

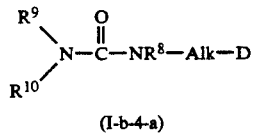

(I-b-4-a)

The reactions of (XI) with (X) and (XII) with (XIII) are conveniently conducted in a suitable reaction-inert solvent, such as, for example, a hydrocarbon, e.g. benzene, methylbenzene; a ketone, e.g. acetone; a halogenated hydrocarbon, e.g. dichloromethane, trichloromethane; an ether, e.g. 1,1'-oxybisethane, tetrahydrofuran and the like; a polar aprotic solvent, e.g. N,N-dimethylacetamide, N,N-dimethylformamide or a mixture of such solvents. An appropriate base such as for example, an alkali metal carbonate, sodium hydride or an organic base such as for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (b-3) and Y is $NR^8$, said compounds being represented by formula (I-b-3-a), may also be prepared by reacting a carboxylic acid of formula (XIV) or a functional derivative with an amine of formula (XIII).

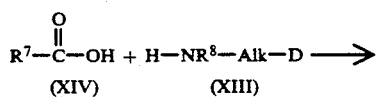

(XIV)           (XIII)

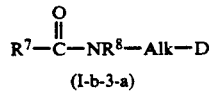

(I-b-3-a)

The reaction of (XIV) with (XIII) may generally be conducted following the same procedures as previously described for the amidation reaction of (V) with (IV).

The compounds of formula (I) wherein L is a radical of formula (b-1) wherein $R^4$ represents cyano, aryl or Het, said radical being represented by $R^{4-a}$ and said compounds by (I-b-1), can also be prepared by the addition reaction of a piperidine of formula (II) with an alkene of formula (XV) in a reaction-inert solvent such as, for example, an aromatic hydrocarbon, e.g. benzene, methylbenzene and the like, an alkanol, e.g. methanol, ethanol, 2-propanol and the like, a ketone, e.g. 2-propanone and the like, an ether, e.g. tetrahydrofuran and the like, or a mixture of such solvents.

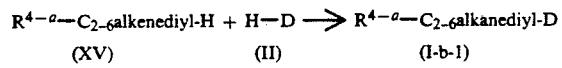

(XV)           (II)           (I-b-1)

The compounds of formula (I) wherein L is a radical of formula (b-2) wherein X is O and $R^5$ is H or $C_{1-6}$alkyl, said radical being represented by $R^{5-b}$ and said compounds by (I-b-2-c) can be prepared by reacting a piperidine of formula (II) with an epoxide of formula (XVI).

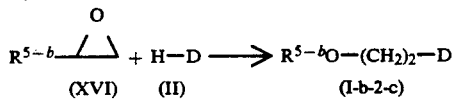

(XVI)           (II)           (I-b-2-c)

The reaction may be conducted by stirring and, if desired, heating the reactants in a reaction-inert solvent such as, for example, water, a ketone, e.g. 2-propanone, 4-methyl-2-pentanone; an ether, e.g. tetrahydrofuran, 1,1'-oxybisethane; an alcohol, e.g. methanol, ethanol, 1-butanol; a dipolar aprotic solvent, e.g. N,N-dimethylformamide, N,N-dimethylacetamide, and the like, or a mixture of such solvents.

The compounds of formula (I) can also be converted into each other following art-known procedures of functional group transformation. Some examples of such procedures will be cited hereinafter.

Compounds of formula (I) containing a hydroxy function may be O-alkylated according to art-known O-alkylation procedures, e.g. by stirring the former with an appropriate alkylating agent, if desired, in the presence of a base and a solvent.

Compounds of formula (I) bearing a protective dioxolan ring may be deacetalized to yield the corresponding oxo compounds. Said deacetalization may be conducted following procedures widely known in the art such as, for example, by reacting the starting materials in an acidic aqueous medium.

The compounds of formula (I) containing a cyano substituent can be converted into the corresponding amines by stirring and, if desired, heating the starting cyano compounds in a hydrogen containing medium in the presence of an appropriate catalyst such as, for example, platinum-on-charcoal, Raney nickel and the like catalysts and optionally in the presence of a base such as, for example, an amine e.g. N,N-diethylethanamine and the like, or a hydroxide, e.g. sodium hydroxide and the like. Suitable solvents are, for example, alkanols, e.g. methanol, ethanol and the like; ethers, e.g. tetrahydrofuran and the like or a mixture of such solvents.

The compounds of formula (I) containing an amino group can also be prepared by treating a carbamate with a base, such as, for example, a hydroxide, e.g. potassium hydroxide, sodium hydroxide and the like. Suitable solvents are alkanols, e.g. methanol, 2-propanol and the like; ethers, e.g. tetrahydrofuran and the like.

Amino groups may be alkylated following art-known procedures such as, for example, N-alkylation, reductive N-alkylation and the like methods, as described hereinbefore.

The compounds of formula (I) containing an ester group may be converted into the corresponding carboxylic acids following art-known saponification procedures, e.g. by treating the starting compound with an aqueous alkaline or an aqueous acidic solution.

The compounds of formula (I) wherein $R^1$ is halo may be converted into compounds wherein $R^1$ is hydrogen following art-known hydrogenolysis procedures, e.g. by stirring and, if desired, heating the starting compounds in a suitable reaction-inert solvent in the presence of hydrogen and an appropriate catalyst such as, for example, palladium-on-charcoal and the like catalysts.

The compounds of formula (I) may also be converted to the corresponding N-oxide forms following art-known procedures for converting a trivalent nitrogen to its N-oxide-form. Said N-oxidation reaction may generally be carried out by reacting the starting material of formula (I) with an appropriate organic or inorganic peroxide. Appropriate inorganic peroxides comprise, for example, hydrogen peroxide, an alkali metal or earth alkaline metal peroxide, e.g. sodium peroxide, potassium peroxide, barium peroxide and the like; appropriate organic peroxides comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like. Said N-oxidation may be carried out in a suitable solvent such as, for example, water, a lower alkanol, e.g. methanol, ethanol, propanol, butanol and the like; a hydrocarbon, e.g. benzene, methylbenzene, dimethylbenzene and the like; a ketone, e.g. 2-propanone, 2-butanone and the like, a halogenated hydrocarbon, e.g. dichloromethane, trichloromethane and the like or mixtures of such solvents. In order to enhance the reaction rate, it may be appropriate to heat the reaction mixture.

Some of the intermediates and starting materials in the foregoing preparations are known compounds while others are novel. They may be prepared according to art-known methodologies of preparing said known or similarly known compounds. Some of which are described in EP-A-0,389,037. The procedures for preparing some other intermediates will be described hereinafter in more detail.

The intermediates of formula (II) may be derived from an appropriately substituted piperidine of formula (XVII) by reacting the latter with a reagent of formula (V) or a functional derivative thereof, following the amidation procedures described for the preparation of (I) starting from (IV) and (V), and subsequently removing of the protective group $P^1$ in the thus obtained intermediate (XVIII) following art-known procedures, e.g. by hydroysis in an acidic or an alkaline medium or by catalytic hydrogenation, depending upon the nature of $P^1$.

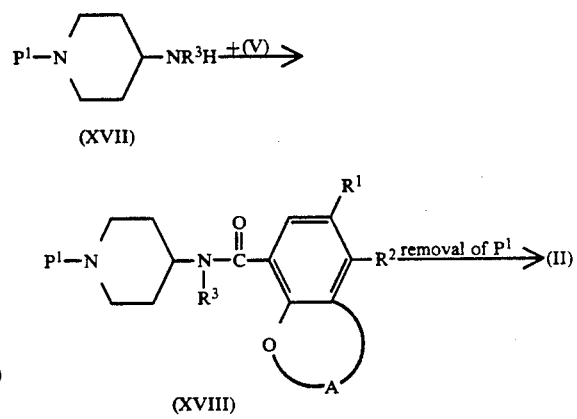

In the reaction of (XVII) with (V) and in the following reaction schemes $P^1$ represents a suitable protective group which is readily removable by hydrogenation or hydrolysis. Preferred protective groups may for example be, hydrogenolyzable groups, e.g. phenylmethyl and the like or hydrolyzable groups, such as $C_{1-4}$alkyloxycarbonyl, e.g. ethoxycarbonyl, benzyloxycarbonyl and the like.

The intermediates of formula (II) wherein $R^3$ is H, said intermediates being represented by formula (II-a), may alternatively be prepared as described in the following reaction scheme. Reaction of an isocyanate of formula (XIX) with an intermediate of formula (XX) yields an intermediate of formula (XVIII) wherein $R^3$ is H, said intermediate being represented by formula (XVIII-a). In formula (XX) $W^5$ is an alkali metal, e.g. lithium, sodium and the like; or halo magnesium e.g. magnesium bromide or magnesium chloride. The reaction can be carried out in a reaction-inert solvent such as, for example, an ether, e.g. tetrahydrofuran, 1,1'-oxybisethane, 1,2-dimethoxyethane and the like; a hydrocarbon, e.g. pentane, hexane and the like. The reaction can be carried out according to reaction procedures as described in Tetrahedron Letters, 27, 1971 (1986) or in J. Org. Chem., 32, 1273 (1967).

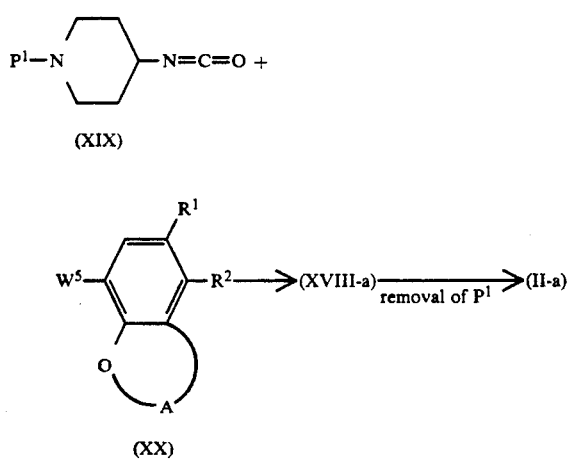

(XIX)

(XX)

The thus obtained intermediates (XVIII-a) can be deprotected as described hereinabove to yield the intermediates of formula (II-a).

The intermediates of formula (IV) can be derived from an appropriately substituted piperidine of formula (XXI) by alkylating the latter with an appropriate reagent L-W (III), following the alkylation procedures described for (I) starting from (II) and (III) and, subsequently removing the protective group $P^1$ in the thus obtained intermediate (XXII) following art-known procedures described hereinbefore.

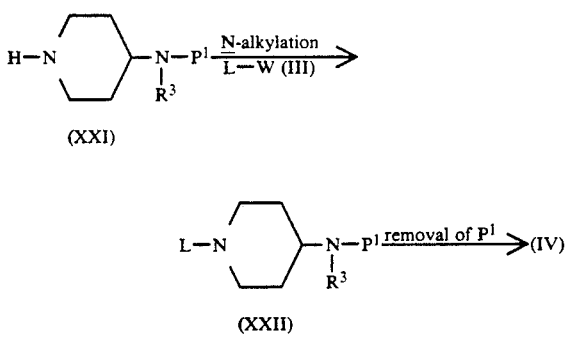

(XXI)

(XXII)

The carboxylic acids of formula (V) can be prepared from intermediates of formula (XXIII), by treating them with an alkyl lithium, e.g. n. butyl lithium, methyl lithium and the like; an alkali metal, e.g. lithium, sodium and the like; a transition metal, e.g. magnesium, zinc, cadmium and the like or an amide, e.g. sodium amide and the like, followed by treatment with $CO_2$ or a reagent of formula $L^1$-C(=O)-$L^1$. $L^1$ represents an appropriate leaving group such as, for example, $C_{1-6}$alkyloxy, halo and the like. In formula (XXIII) $W^6$ represents hydrogen or an appropriate reactive leaving group such as, for example, halo, e.g. chloro, bromo or iodo.

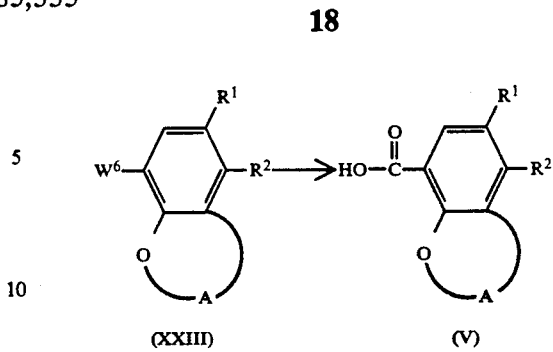

(XXIII)  (V)

Said reaction can conveniently be carried out in a reaction-inert solvent such as for example, an aliphatic hydrocarbon, e.g. pentane, hexane, cyclohexane and the like; an aromatic solvent, e.g. benzene, chlorobenzene and the like; an ether, e.g. tetrahydrofuran, 1,4-dioxane and the like or a mixture of such solvents and optionally in the presence of an amine, e.g. ethanamine, N,N-diethylethanamine, N,N,N',N'-tetramethylethylendiamine and the like.

The intermediates of formula (XXIII) wherein $W^6$ is a reactive leaving group, said $W^6$ being represented by $W^{6-a}$ and said intermediates being represented by (XXIII-a), can in turn be obtained from (XXIV) following art-known halogenation procedures optionally followed by the separation of the undesired isomers.

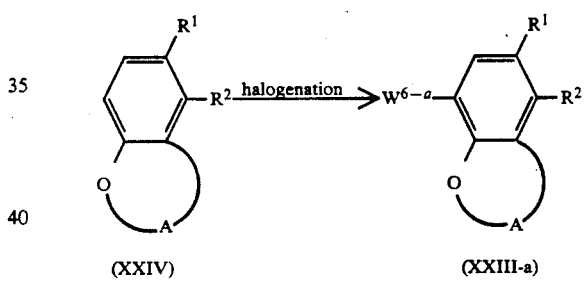

(XXIV)  (XXIII-a)

For example, an intermediate of formula (XXIV) can be halogenated with a dihalide, e.g. chlorine, bromine and the like, optionally in the presence of a catalyst such as, a Lewis acid, e.g. ferric chloride, ferric bromide, aluminum chloride and the like. Intermediate (XXIV) can also be halogenated with N-haloamides, e.g. N-chlorosuccinimide, N-bromosuccinimide and the like. In some instances the reaction can be catalyzed by the addition of acids, e.g. acetic acid, hydrochloric acid and the like. Said halogenation reactions can conveniently be carried out in a reaction-inert solvent such as, for example, water, an aliphatic hydrocarbon, e.g. pentane, hexane, cyclohexane and the like; an aromatic solvent, e.g. benzene, methylbenzene and the like; a halogenated hydrocarbon, e.g. dichloromethane, tetrachloromethane and the like; an ether, e.g. 1,1'-oxybisethane, tetrahydrofuran and the like; or a dipolar aprotic solvent, e.g. acetonitrile and the like.

The intermediates of formula (XXIV) wherein $R^1$ is other than hydrogen, said $R^1$ being represented by $R^{1-a}$ and said intermediates by (XXIV-a), can be prepared by halogenation of an intermediate of formula (XXV).

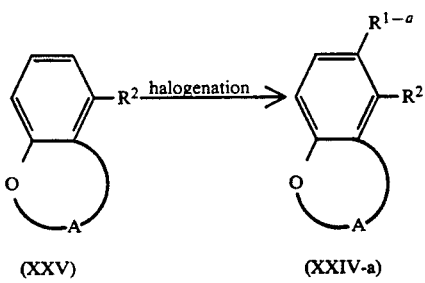

(XXV)    (XXIV-a)

The halogenation reaction can be carried out according to the halogenation procedures described hereinabove for the halogenation of (XXIV).

The starting materials of formula (XXV) can be obtained by cyclizing an intermediate of formula (XXVI) in the presence of boron tribromide or an acid such as, for example, hydrochloric acid, hydrobromic acid and the like, or mixtures of these acids with acetic acid.

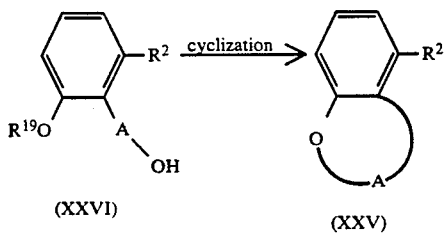

(XXVI)    (XXV)

In intermediate (XXVI) and throughout the following description and reaction schemes $R^{19}$ is $C_{1-4}$alkyl.

The intermediates of formula (XXVI), in turn, can be prepared by deprotecting the functionalized alcohol in intermediate (XXVII).

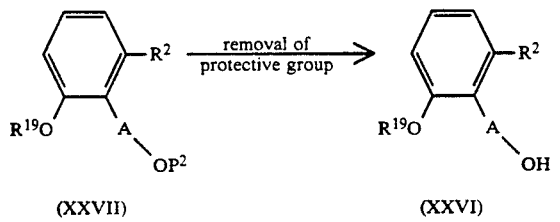

(XXVII)    (XXVI)

In formula (XXVII) $P^2$ is a protective group such as for example, tetrahydropyranyl, tertiairy butyl, phenylmethyl and the like. These protective groups are readily removable by hydrolysis with for example, an acid, e.g. hydrochloric acid, hydrobromic acid, acetic acid and the like or by catalytic hydrogenation in the presence of hydrogen and an appropriate catalyst. In case $R^2$ is amino, it may be expedient to protect this group during the course of the above and the following reactions to avoid undesired side reactions. Suitable protective groups are, for example, $C_{1-6}$alkylcarbonyl, $C_{1-6}$alkyloxycarbonyl, benzyloxycarbonyl and arylmethyl groups. The removal of the protective group may generally be carried out by deblocking, for example, a $C_{1-6}$alkylcarbonyl group with an appropriate acid or base in an anhydric or aqueous organic solvent or in water; or by catalytic hydrogenation in the presence of hydrogen and an appropriate catalyst depending upon the nature of the protective group.

The intermediates of formula (XXVII) can be obtained by reduction of an intermediate of formula (XXVIII).

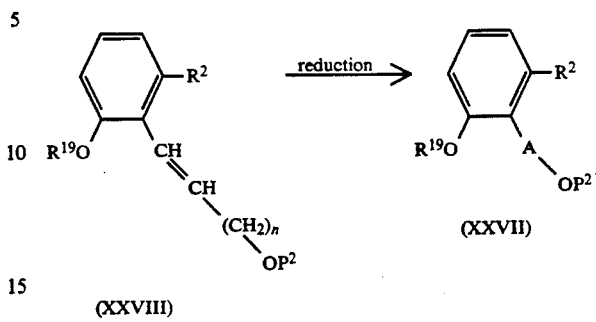

(XXVIII)    (XXVII)

It is to be understood that in formula (XXVIII) and the subsequent formulae one or two hydrogen atoms of the carbon chain may be replaced by a $C_{1-6}$alkyl radical, and n can be 0, 1 or 2. The double bond of formula (XXVIII) may be reduced by catalytic hydrogenation in a suitable solvent, e.g. methanol or ethanol and the like in the presence of hydrogen and an appropriate catalyst e.g. platinum-on-charcoal, palladium-on-charcoal, Raney nickel and the like, optionally at an increased temperature and/or pressure.

The intermediates of formula (XXVIII) can be prepared by reacting an aldehyde (XXIX) with a suitable ylide such as, for example, a phosphorus ylide (e.g. $R^{20}$ and $R^{21}$ are aryl or alkyl: Wittig reaction) or an ylide prepared from a phosphonate (e.g. $R^{20}$ is alkyloxy and $R^{21}$ is $O^-$: Horner-Emmons reaction).

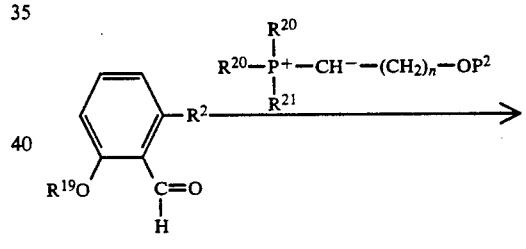

(XXIX)

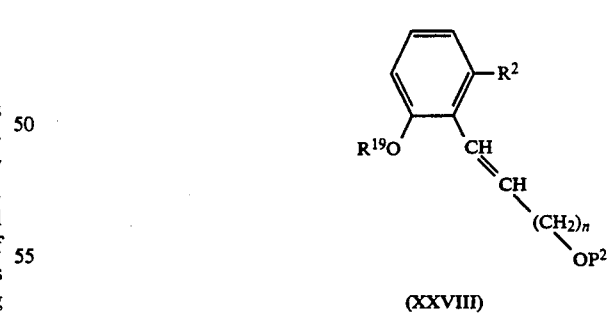

(XXVIII)

Said ylide can be obtained by treating a phosphonium salt or a phosphonate with an appropriate base such as, for example, potassium tert. butoxide, n.butyl lithium, sodium amide, sodium hydride and the like bases under an inert atmosphere and in a reaction-inert solvent such as, for example, an ether, e.g. tetrahydrofuran, 1,4-dioxane and the like.

The intermediates of formula (XXIX) can conveniently be obtained from an alkyloxybenzene derivative of formula (XXX) following art-known formylation procedures, optionally followed by the separation of the undesired isomers.

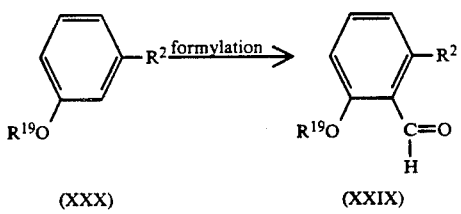

(XXX)  (XXIX)

For example, the alkyloxybenzene derivative of formula (XXX) can be formylated by reaction with an appropriate base such as, for example, an alkyl lithium, e.g. methyl lithium, n.butyl lithium, and the like, and subsequently reacting the thus obtained metalated alkyloxybenzene derivative with a formamide, e.g. N,N-dimethylformamide, N-methyl-N-phenylformamide, and the like. Said formylation may also be conducted under Vilsmeier-Haack (phosphoryl chloride, formamide) or Gattermann (zinc(II)-cyanide, hydrochloric acid) conditions in an acidic medium.

Alternatively, the starting materials of formula (XXV), wherein A is —CH$_2$—CH$_2$—, wherein one or two hydrogen atoms may be replaced by C$_{1-6}$alkyl, said intermediates being represented by formula (XXV-a-1), can be obtained by cyclizing an intermediate of formula (XXVI-a-1) in an acidic medium according to the procedures described in J. Het. Chem., 17, 1333 (1980).

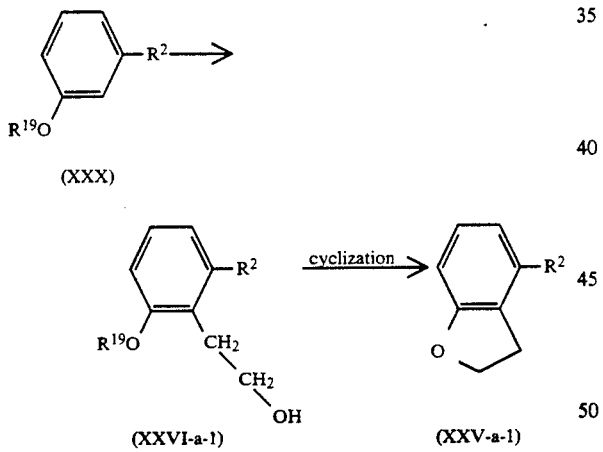

(XXX)

(XXVI-a-1)  (XXV-a-1)

It is to be understood that in formula (XXVI-a-1) and (XXV-a-1) one or two hydrogen atoms of the ethyl or tetrahydrofuran moiety may be replaced by a C$_{1-6}$alkyl radical.

The desired intermediates of formula (XXVI-a-1) can be obtained from an alkyloxybenzene derivative of formula (XXX) by reacting the latter with an ethylene oxide derivative in a reaction inert solvent such as, for example, an ether, e.g. tetrahydrofuran, 1,4-dioxane, and the like in the presence of a base. Appropriate bases are, for example, alkyl lithium, e.g. methyl lithium, n.butyl lithium and the like.

The intermediates of formula (V) can also be prepared by hydrolyzing the ester group of formula (XXXI) in a basic or acidic aqueous medium.

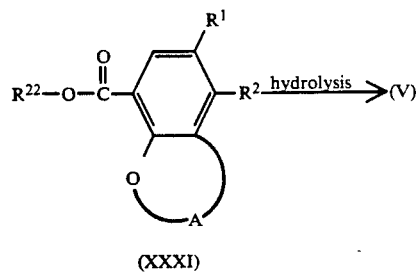

(XXXI)

In (XXXI) and throughout the following description and reaction schemes R$^{22}$ is a C$_{1-4}$alkyl radical.

The above esters of formula (XXXI) in turn can be obtained by halogenation of the intermediates of formula (XXXII) according to the procedures described hereinbefore for the preparation of the intermediates of formula (XXIII-a) from (XXIV).

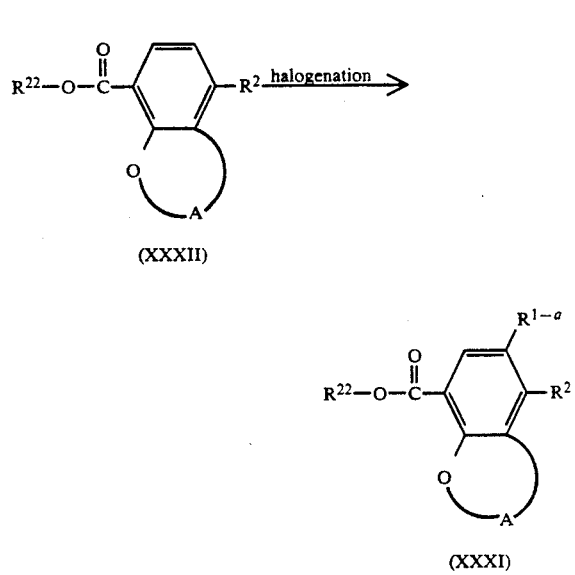

(XXXII)

(XXXI)

The intermediates of formula (XXXII), wherein A is -C(CH$_3$)$_2$-CH$_2$-, said intermediates being represented by formula (XXXII-a-1) can be obtained by cyclizing the phenyl allyl intermediate (XXXIII), in the presence of an acid, for example, formic acid, acetic acid, hydrogen bromide and the like, or a mixture of these acids.

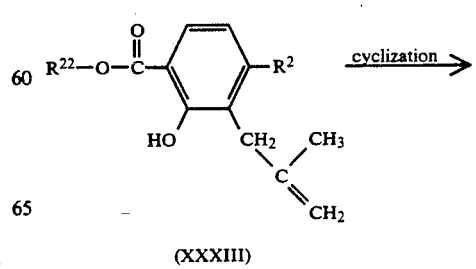

(XXXIII)

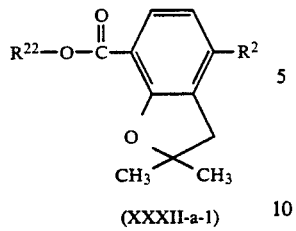

(XXXII-a-1)

The above phenyl allyl intermediate (XXXIII) can be prepared by a Claisen rearrangement of a phenyl allyl ether of formula (XXXIV).

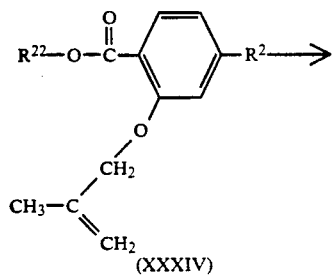

(XXXIV)

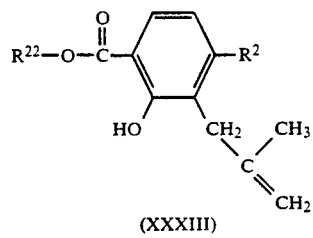

(XXXIII)

Said reaction can be carried out in a reaction-inert solvent at a somewhat elevated temperature, in particular the reflux temperature of the reaction mixture. Suitable solvents are, for example, aliphatic or aromatic hydrocarbons, e.g. methylbenzene, phenylbenzene and the like, halogenated hydrocarbons, e.g. chlorobenzene and the like, alcohols, e.g. cyclohexanol and the like, ethers, e.g. 1,1′-oxybisethane, 1,1′-oxybisbenzene and the like, amines, e.g. N,N-dimethylaniline and the like; dipolar aprotic solvents, e.g. N,N-dimethylformamide, 1-methyl-2-pyrrolidinone and the like.

The phenyl allyl ether of formula (XXXIV) can in turn be prepared by the O-alkylation reaction of a phenol intermediate of formula (XXXV) with an alkylating reagent of formula (XXXVI) following art-known O-alkylation procedures.

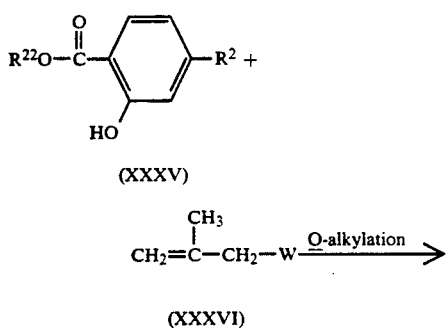

(XXXV)

(XXXVI)

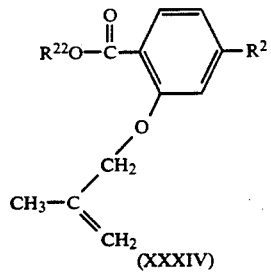

(XXXIV)

In formula (XXXVI) W is defined as described hereinbefore for intermediate (III). Said O-alkylation reaction can conveniently be carried out by mixing the reactants, optionally in a reaction-inert solvent such as, for example, water; an aromatic solvent, e.g. benzene and the like; a $C_{1-6}$alkanol, e.g. ethanol and the like; a ketone, e.g. 2-propanone and the like; an ether, e.g. tetrahydrofuran and the like; or a dipolar aprotic solvent, e.g. N,N-dimethylformamide and the like. The addition of an appropriate base such as, for example potassium carbonate, sodium hydroxide or sodium hydride and the like may optionally be used to pick up the acid which is formed during the course of the reaction.

The intermediates of formula (XXXI), wherein A is —$CH_2$—$CH_2$—$CH_2$—, wherein one or two hydrogen atoms may be replaced by $C_{1-6}$alkyl, said intermediates being represented by formula (XXXI-a-2), can be obtained by reduction of a 2H-benzopyran of formula (XXXVII) following the reduction procedures described hereinbefore for the preparation of the intermediates of formula (XXVII).

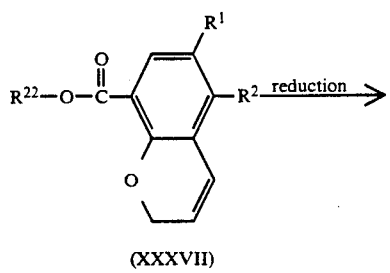

(XXXVII)

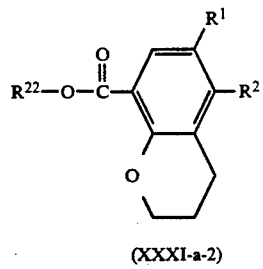

(XXXI-a-2)

It is to be understood that in formula (XXXI-a-2) and the subsequent formulae (XXXVII) and (XXXVIII) one or two hydrogen atoms of the pyran moiety or the carbon chain may be replaced by $C_{1-6}$alkyl.

The intermediates of formula (XXXVII) can be prepared by a Claisen rearrangement of a phenylether of formula (XXXVIII) followed by a cyclization reaction.

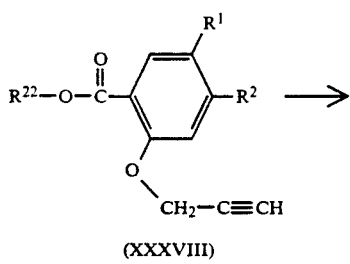

(XXXVIII)

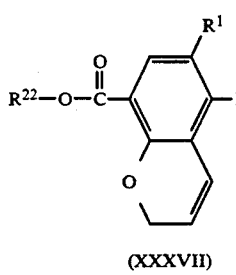

(XXXVII)

Said reaction can be carried out according to reaction procedures as described in Elderfield, Heterocyclic Compounds, Vol. 2, pages 393–418. Preferably the rearrangement is carried out in a reaction-inert solvent at temperatures above 100° C. Suitable solvents are for example, hydrocarbons, e.g. phenylbenzene, diphenylmethane, naphthalene, decahydronaphthalene and the like; halogenated hydrocarbons, e.g. chlorobenzene and the like; alcohols, e.g. cyclohexanol and the like; ethers, e.g. 1,1'-oxybisbenzene and the like; or dipolar aprotic solvents, e.g. N,N-dimethylacetamide, N,N-dimethylformamide and the like.

The above described intermediates can also be converted into each other following art-known procedures of functional group transformation as described hereinbefore for the compounds of formula (I).

The intermediates of formula (II) and (XVIII) wherein $R^1$, $R^2$, $R^3$, A and $P^1$ have the above described meanings are deemed to be novel, and as such they represent an additional feature of the present invention.

The compounds of formula (I) may have asymmetric carbon atoms in their structure. The absolute configuration of these centres may be indicated by the stereochemical descriptors R and S. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms, as well as mixtures thereof, are obviously intended to be embraced within the scope of the invention.

The compounds of formula (I) containing an alkene moiety may be present in a "E" or "Z" form, said E- and Z-notation having the meanings described in J. Org. Chem., 35, 2849–2868 (1970).

Stereochemically isomeric forms of the intermediates described in the foregoing reaction schemes and of the compounds of formula (I) may be obtained by the application of art-known procedures. For example, diastereoisomers may be separated by physical separation methods such as destillation, selective crystallization, chromatographic techniques, e.g. counter current distribution, liquid chromatography and the like techniques. Pure enantiomers may be obtained by separating the corresponding racemates for example, by the selective crystallization of their diastereomeric salts with optically active resolving agents, chromatography of diastereomeric derivatives, chromatography of the racemate over a chiral stationary phase and the like techniques. Alternatively, enantiomerically pure forms can conviently be obtained from the enantiomerically pure isomeric forms of the appropriate starting materials, provided that the subsequent reactions occur stereospecifically.

The compounds of formula (I) and the intermediates of formula (II), the N-oxide forms, the pharmaceutically acceptable salts and possible stereoisomeric forms thereof possess favourable gastrointestinal motility stimulating properties. In particular the present compounds show significant motility enhancing effects on the colon. The latter property is clearly evidenced by the results obtained in the "colon ascendens induced contractions" test described hereinafter.

The stimulatory effect of the subject compounds of formula (I) and (II) on the motility of the gastrointestinal system may further be evidenced by, for example, the various test models described in The Journal of Pharmacology and Experimental Therapeutics, 234, 775–783 (1985) and in Drug Development Research 8, 243–250 (1986). The "Gastric emptying of a liquid meal in rats" test, the "Gastric emptying of an acaloric meal in conscious dog after administration of lidamidine" test and the "Amplification of contractions induced by transdermal stimulation of Guinea pig ileum" test, all of which are described in the above mentioned articles, further revealed that a representative number of compounds also significantly accelerated gastric emptying.

In addition, the present compounds of formula (I) and (II), the N-oxide forms, the pharmaceutically acceptable acid addition salts and possible stereoisomeric forms thereof have a particular receptor binding profile. Some groups of compounds within the present invention, particularly those wherein the radical A is not substituted with $C_{1-6}$alkyl have a poor $5HT_3$ antagonistic activity. Most compounds of the invention do not show any apparent marked receptor-binding affinity with serotonergic-$5HT_1$ and serotonergic-$5HT_2$ receptors and have little or no dopaminergic antagonistic activity.

In view of their useful gastrointestinal motility enhancing properties the subject compounds may be formulated into various forms for administration purposes.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of their capability to stimulate the motility of the gastrointestinal system and, in particular their capacity to enhance the motility of the colon, the subject compounds are useful to normalize or to improve the gastric and intestinal emptying in subjects suffering from a disturbed motility, e.g. a decreased peristalsis of the stomach and/or of the small and/or large intestine.

In view of the utility of the compounds of the present invention, there is provided a method of treating warm-blooded animals suffering from motility disorders of the gastrointestinal system such as, for example, gastroparesis, flatulent dyspepsia, non-ulcer dyspepsia, pseudo-obstruction, and in particular impaired colonic transit. Said method comprises the systemic administration of an effective gastrointestinal motor-stimulating amount of a compound of formula (I), a N-oxide, a pharmaceutically acceptable acid addition salt or a possible stereoisomeric form thereof, to warm-blooded animals. Some particular compounds of the invention also posses therapeutic value in the treatment of upper bowel motility and gastroesophageal reflux disorders.

Those of skill in the pertinent art could easily determine the effective motor-stimulating amount from the test results presented hereinafter. In general it is contemplated that an effective amount would be from 0.001 mg/kg to 10 mg/kg body weight, and more preferably from 0.01 mg/kg to 1 mg/kg body weight.

The following examples are intended to illustrate and not to limit the invention in all its aspects. Unless otherwise stated all parts therein are by weight.

EXPERIMENTAL PART

A. Preparation of the Intermediates

Example 1 a) To a solution of 310 parts of methyl 4-(acetylamino]-2-hydroxybenzoate in 2820 parts of N,N-dimethylformamide there were added portionwise 71 parts of a dispersion of sodium hydride in mineral oil (50%) and, after stirring for 1 hour at room temperature, one crystal of potassium iodide and 172 parts of 3-chloro-3-methyl-1-butyne under a nitrogen atmosphere. The whole was stirred for 24 hours at 90° C. and was then poured into NaOH 10% (aq.). The product was extracted with dichloromethane and the extract was dried, filtered and evaporated. The residue was successively stirred in petroleumether and dissolved in dichloromethane. The latter solution was washed with water, NaOH 10% and water and was then dried, filtered and evaporated. The residue was purified by column chromatography (silica gel; $CH_2Cl_2$). The eluent of the desired fraction was evaporated, yielding in two fractions 41 parts (10.1%) of methyl 4-(acetylamino)-2-(1,1-dimethyl-2-propynyloxy)benzoate (interm. 1).

b) A mixture of 36 parts of intermediate 1 and 188 parts of N,N-dimethylacetamide was stirred for 24 hours at reflux temperature. The reaction mixture was evaporated and the residue was dissolved in dichloromethane. This solution was washed with water, NaOH 5% and water and was then dried, filtered and evaporated. The residue was purified by column chromatography (silica gel; $CH_2Cl_2/CH_3OH$ 99:1). The eluent of the desired fraction was evaporated, yielding 23.7 parts (66.2%) of methyl 5-(acetylamino)-2,2-dimethyl-2H-1-benzopyran-8-carboxylate (interm. 2).

c) A mixture of 23.7 parts of intermediate 2 and 198 parts of methanol was hydrogenated overnight at normal pressure and room temperature with 2 parts of palladium-on-charcoal catalyst 10%. After the calculated amount of hydrogen was taken up, the catalyst was filtered off and the filtrate was evaporated, yielding 21.2 parts (88.9%) of methyl 5-(acetylamino)-3,4-dihydro-2,2-dimethyl-2H-1-benzopyran-8-carboxylate (interm. 3).

d) A mixture of 21.2 parts of intermediate 3; 10.3 parts of N-chlorosuccinimide and 158 parts of acetonitrile was stirred for 2 hours at reflux temperature. The reaction mixture was evaporated and the residue was dissolved in dichloromethane. This solution was washed with water, dried, filtered and evaporated. The residue was purified by column chromatography (silica gel; $CH_2Cl_2/CH_3OH$ 99:1). The eluent of the desired fraction was evaporated, yielding 23 parts (95.8%) of methyl 5-(acetylamino)-6-chloro-3,4-dihydro-2,2-dimethyl-2H-1-benzopyran-8-carboxylate (interm. 4).

e) A mixture of 20 parts of intermediate 4; 36 parts of potassium hydroxide and 250 parts of water was stirred for 16 hours at reflux temperature. After cooling, the solvent was decanted and the residue was washed with dichloromethane (2x). The aqueous layer was acidified with 69.9 parts of HCl (conc.). The precipitate was filtered off, washed with water and dried in vacuo at 70° C., yielding 13 parts (79.4%) of 5-amino-6-chloro-3,4-dihydro-2,2-dimethyl-2H-1-benzopyran-8-carboxylic acid; mp. 165° C. (interm. 5).

Example 2 a) A mixture of 58 parts of methyl 4-(acetylamino)-2,3-dihydro-2,2-dimethyl-7-benzofurancarboxylate, 123 parts of potassium hydroxide and 1100 parts of water was stirred for 3 hours at reflux temperature. After cooling, the reaction mixture was acidified to pH 1 with HCl. The precipitate was filtered off and dried in vacuo at 80° C., yielding 36 parts (79.0%) of 4-amino-2,3-dihydro-2,2-dimethyl-7-benzofurancarboxylic acid (interm. 6).

b) A mixture of 36 parts of intermediate 6; 66.2 parts of sulfuric acid and 142 parts of methanol was stirred for ½ hour at reflux temperature. After cooling, the reaction mixture was basified with methanol saturated with ammonia, and was then evaporated. The residue was partitioned between dichloromethane and water. The organic layer was separated, washed with water, dried, filtered and evaporated. The residue was crystallized from acetonitrile at 0° C. The product was filtered off and dried in vacuo at 40° C., yielding 20 parts (53.2%) of methyl 4-amino-2,3-dihydro-2,2-dimethyl-7-benzofurancarboxylate (interm. 7).

c) A mixture of 15.3 parts of intermediate 7; 23.3 parts of 2-iodopropane, 9.13 parts of N,N-diethylethanamine and 72.1 parts of hexamethylphosphoric triamide was stirred for 28 hours at 130° C. After cooling, the reaction mixture was poured into water. The product was extracted with dichloromethane and the extract was washed with water, dried, filtered and evaporated. The residue was purified by column chromatography (silica gel; $CH_2Cl_2/CH_3OH$ 99:1). The eluent of the desired fraction was evaporated and the residue was crystallized from 2,2'-oxybispropane at 0° C. The product was filtered off and dried in vacuo at 40° C. yielding 10 parts (54.2%) of methyl 2,3-dihydro-2,2-dimethyl-4-[(1-methylethyl)amino]-7-benzofurancarboxylate (interm. 8).

d) A mixture of 9 parts of intermediate 8; 3.2 parts of sodium hydroxide and 60 parts of water was stirred for 1 hour at reflux temperature. After cooling, the reaction mixture was acidified to pH 6 with HCl (conc.). The precipitate was filtered off, washed with water and dried in vacuo at 60° C., yielding 7.2 parts (76.0%) of 2,3-dihydro-2,2-dimethyl-4-[(1-methylethyl)amino]-7-benzofurancarboxylic acid (interm. 9).

Example 3 a) To a suspension of 17.0 parts of 4-amino-5-chloro-2,3-dihydro-7-benzofurancarboxylic acid (prepared as described in EP-A-0,389,037) in 435 parts of trichloromethane there were added successively 9.13 parts of N,N-diethylethanamine and 8.68 parts of ethyl chloroformate, keeping the temperature below 5° C. After stirring for 2 hours while cooling on ice, the whole was added to a solution of 14.5 parts of ethyl 4-amino-1-piperidinecarboxylate in 218 parts of trichloromethane at a temperature below 5° C. Stirring was continued overnight at room temperature. The reaction mixture was washed with NaOH 5% (2x) and with water (2x) and was then dried, filtered and evaporated. The residue was successively triturated with 2,2'-oxybispropane (3x) and crystallized from acetonitrile. The product was filtered off, washed with acetonitrile and dried, yielding 19.7 parts (66.9%) of product. An additional amount of 1.2 parts (4.1%) was obtained from the combined 2,2'-oxybispropane layers. Total yield: 20.9 parts (71%) of ethyl 4-[[(4-amino-5-chloro-2,3-dihydro-7-benzofuranyl)carbonyl]amino]-1-piperidine-carboxylate; mp. 158.6° C. (interm. 10).

b) A solution of 18.4 parts of intermediate 10 and 28.0 parts of potassium hydroxide in 125 parts of 2-propanol was stirred for 4 hours at reflux temperature. The solvent was evaporated and replaced by 100 parts of water. The mixture was evaporated again and the residue was stirred in 100 parts of water for 15 min. while heating on a water-bath. After cooling, the solid was filtered off, washed with water and dissolved in boiling 2-propanol. There were added 400 parts of water to the solution. The product crystallized upon cooling and was filtered off, washed with water and dried, yielding 12.35 parts (83.5%) of 4-amino-5-chloro-2,3-dihydro-N-(4-piperidinyl)-7-benzofurancarboxamide; mp. 190.3° C. (interm. 11).

All intermediates listed in Table 1 were prepared in a similar manner.

TABLE 1

| Int. No. | $R^1$ | $R^2$ | —O—A— | Physical data (mp.) |
|---|---|---|---|---|
| 11 | Cl | $NH_2$ | —O—$(CH_2)_2$— | 190.3° C. |
| 12 | Cl | $NH_2$ | —O—$(CH_2)_3$— | 158.5° C. |
| 13 | Cl | $NH_2$ | —O—$C(CH_3)_2$—$CH_2$— | 137.5° C. |
| 14 | Cl | $NH_2$ | —O—$C(CH_3)_2$—$(CH_2)_2$— | 170.8° C. |
| 15 | Cl | H | —O—$C(CH_3)_2$—$CH_2$— | 173.6° C. |
| 16 | Cl | H | —O—$(CH_2)_2$— | — |
| 17 | Cl | H | —O—$C(CH_3)_2$—$(CH_2)_2$— | 126.3° C. |
| 18 | H | NH—$CH(CH_3)_2$ | —O—$C(CH_3)_2$—$CH_2$— | — |

Example 4

To a stirred and cooled (ice-bath) mixture of 20 parts of (−)-(R)-tetrahydro-2-furanmethanol and 39.2 parts of pyridine there were added dropwise 24.7 parts of methanesulfonyl chloride. Stirring at room temperature was continued for 16 hours. To the reaction mixture there was added dichloromethane and the whole was washed with HCl 1N, dried, filtered and evaporated. The residue was purified by column chromatography (silica gel; $CH_2Cl_2/CH_3OH$ 99.5:0.5). The eluent of the desired fraction was evaporated, yielding 26.7 parts (75.6%) of (−)-(R)-tetrahydro-2-furanmethanol methanesulfonate(ester); $[\alpha]_D^{20}= -15.78°$ (conc.=1% in $CH_2Cl_2$) (interm. 19).

In a similar manner there was also prepared: (+)-(S)-tetrahydro-2-furanmethanol methanesulfonate(ester); $[\alpha]_D^{20}= +16.17°$ (conc.=1% in $CH_2Cl_2$) (interm. 20).

Example 5

To a solution of 10 parts of 3-(cyclohexyloxy)-1-propanol in 160 parts of dichloromethane there were added 11.2 parts of N,N-diethylethanamine and dropwise 8.14 parts of methanesulfonyl chloride. The whole was stirred for 9 hours at room temperature. The reaction mixture was washed with $Na_2CO_3$ (aq.) and water and was then dried, filtered and evaporated. The residue was purified by column chromatography (silica gel; $CH_2Cl_2/CH_3OH$ 99:1). The eluent of the desired fraction was evaporated and the residue was co-evaporated with methylbenzene. The product was filtered off and dried, yielding 8.6 parts (57.8%) of 3-(cyclohexyloxy)-1-propanol methanesulfonate (ester) (interm. 21).

Example 6

A solution of 5.5 parts of 3,3-bis(4-fluorophenyl)-1-propanol and 2.92 parts of thionyl chloride in 39.9 parts of dichloromethane was stirred for 4 hours at 60° C. The reaction mixture was evaporated and then co-evaporated with methylbenzene. The residue was dissolved in ethyl acetate and this solution was washed with $Na_2CO_3$ (aq.), water and NaCl (sat.) and was then dried, filtered and evaporated. The residue was purified by column chromatography (silica gel; $(C_2H_5)_2O$/n-hexane 2:98). The eluent of the desired fraction was evaporated, yielding 4.5 parts (76.7%) of 1-[3-chloro-1-(4-fluorophenyl)propyl]-4-fluorobenzene(interm.22).

B. Preparation of the Final Compounds

Example 7

A solution of 2.96 parts of intermediate 11; 3.2 parts of sodium carbonate and 160 parts of 4-methyl-2-pentanone was stirred for ½ hour at reflux temperature using a water separator. There were added 3.6 parts of tetrahydro-2-furanmethanol methanesulfonate (ester) and stirring at reflux temperature was continued for 48 hours. The reaction mixture was taken up in dichloromethane and this solution was washed with water, dried, filtered and evaporated. The residue was purified by column chromatography (silica gel; $CH_2Cl_2/CH_3OH$ 95:5). The eluent of the desired fraction was evaporated and the residue was crystallized from acetonitrile. The product was filtered off and dried, yielding 1.63 parts (42.9%) of 4-amino-5-chloro-2,3-dihydro-N-[1-[(tetrahydro-2-furanyl)methyl]-4-piperidinyl]-7-benzofurancarboxamide; mp. 175.4° C. (comp. 3).

Example 8

A mixture of 3.09 parts of intermediate 12; 3.18 parts of sodium carbonate and 160 parts of 4-methyl-2-pentanone was stirred at reflux temperature using a water separator. There were added 2.74 parts of 6-(2-chloroethyl)-7-methyl-5H-thiazolo[3,2-a]-pyrimidin-5-one and 0.1 parts of potassium iodide and stirring at reflux temperature was continued for 36 hours. The reaction mixture was evaporated and the residue was partitioned between trichloromethane and water. The organic layer was separated, washed with water, dried, filtered and evaporated. The residue was purified by column chromatography (silica gel; $CH_2Cl_2/CH_3OH$ 90:10). The eluent of the desired fraction was evaporated and the residue was boiled in acetonitrile. After cooling, the product was filtered off and dried, yielding 2.7 parts (53.8%) of 5-amino-6-chloro-3,4-dihydro-N-[1-[2-(7-methyl-5-oxo-5H-thiazolo[3,2-a]pyrimidin-6-yl)ethyl]-4-piperidinyl]-2H-1-benzopyran-8-carboxamide; mp. 211.8° C. (comp. 2).

Example 9

A mixture of 21.7 parts of intermediate 12; 5.7 parts of chloroacetonitrile, 9.2 parts of N,N-diethylethanamine and 430 parts of N,N-dimethylformamide was stirred overnight at 60° C. The reaction mixture was evaporated and to the residue there was added $Na_2CO_3$ (aq.). The product was extracted with dichloromethane (3x) and the combined extracts were dried, filtered and evaporated. The residue was suspended in acetonitrile. A first fraction of the product was filtered off and the filtrate was evaporated. The residue was purified by column chromatography (silica gel; $CH_2Cl_2/CH_3OH(NH_3)$ 97:3). The eluent of the desired fractions was evaporated and the residue was stirred in acetonitrile. A second fraction of the product was obtained and the combined fractions were dried in vacuo, yielding 22.1 parts (90.5%) of 5-amino-6-chloro-N-[1-(cyanomethyl)-4-piperidinyl]-3,4-dihydro-2H-1-benzopyran-8-carboxamide; mp. 194° C. (comp. 10).

Example 10

A mixture of 4.3 parts of 2-(3-chloropropyl)-2-methyl-1,3-dioxolane, 7.4 parts of intermediate 13; 4.7 parts of N,N-diethylethanamine, a catalytic amount of potassium iodide and 106 parts of N,N-dimethylformamide was stirred for 17 hours at 70° C. The reaction mixture was evaporated and to the residue there was added $Na_2CO_3$ (aq.). The product was extracted with dichloromethane and the extract was dried, filtered and evaporated. The residue was purified by column chromatography (silica gel; $CH_2Cl_2/CH_3OH(NH_3)$ 97:3). The eluent of the desired fraction was evaporated and the residue was triturated in 2,2'-oxybispropane. The product was filtered off and dried, yielding 2.1 parts (20.2%) of 4-amino-5-chloro-2,3-dihydro-2,2-dimethyl-N-[1-[3-(2-methyl-1,3-dioxolan-2-yl)propyl]-4-piperidinyl]-7-benzofurancarboxamide; mp. 136.5° C. (comp. 8).

Example 11

A mixture of 6 parts of intermediate 14; 1.13 parts of 2-propenenitrile and 78 parts of 2-propanol was stirred for 4 hours at reflux temperature. The reaction mixture was evaporated and the residue was suspended in 2,2'-oxybispropane. The precipitate was filtered off and dried in vacuo at 60° C., yielding 6.8 parts (96.6%) of 5-amino-6-chloro-N-[1-(2-cyanoethyl)-4-piperidinyl]-3,4-dihydro-2,2-dimethyl-2H-1-benzopyran-8-carboxamide (comp. 25).

Example 12

A mixture of 22 parts of compound 10 in 356 parts of tetrahydrofuran and 79 parts of methanol was reduced at normal pressure and room temperature with 6 parts of Raney nickel. After completion of the reaction, the catalyst was filtered off and the filtrate was evaporated. The residue was purified by column chromatography (silica gel; CH$_2$Cl$_2$/CH$_3$OH(NH$_3$) 93:7). The eluent of the desired fraction was evaporated and the residue was successively triturated in 2,2′-oxybispropane and stirred in a small amount of acetonitrile. The product was filtered off and dried, yielding 14 parts (63.0%) of 5-amino-N-[1-(2-aminoethyl)-4-piperidinyl]-6-chloro-3,4-dihydro-2H-1-benzopyran-8-carboxamide; mp. 130° C. (comp. 11).

Example 13

A mixture of 16.7 parts of compounds 55; 19 parts of potassium hydroxide and 92 parts of 2-propanol was stirred for 3 hours at reflux temperature. The reaction mixture was evaporated and the residue was co-evaporated with water (2x) and then partitioned between dichloromethane, methanol and water. The aqueous layer was separated and reextracted with dichloromethane. The combined organic layers were dried, filtered and evaporated. The residue was crystallized from water. The product was filtered off and dried, yielding 8.3 parts (65.1%) of N-[1-(3-aminopropyl)-4-piperidinyl]-5-chloro-2,3-dihydro-2,2-dimethyl-7-benzofurancarboxamide hemihydrate; mp. 123.1° C. (comp. 71).

Example 14

To a cooled (ice-bath) mixture of 2.3 parts of compound 11 and 74 parts of trichloromethane there were added 0.86 parts of N,N-diethylethanamine and dropwise a solution of 0.77 parts of ethyl chloroformate in 40 parts of trichloromethane, keeping the temperature below 10° C. After stirring for ½ hour at room temperature, the reaction mixture was washed with water, dried, filtered and evaporated. The residue was purified by column chromatography (silica gel; CH$_2$Cl$_2$/CH$_3$OH(NH$_3$) 95:5). The eluent of the desired fraction was evaporated and the residue was crystallized from acetonitrile. The product was filtered off and dried, yielding 1.4 parts (50.7%) of ethyl [2-[4-[[(5-amino-6-chloro-3,4-dihydro-2H-1-benzopyran-8-yl)carbonyl]amino]-1-piperidinyl]-ethyl]carbamate; mp. 160.3° C. (comp. 16).

Example 15

A mixture of 3.67 parts of compound 14; 1.85 parts of 2-chloro-1H-benzimidazole, 4.7 parts of N,N-dimethylacetamide, a catalytic amount of potassium iodide and 2.10 parts of sodium carbonate was stirred for 3 hours at 120° C. After cooling, the reaction mixture was diluted with water. The product was extracted with dichloromethane (2x) and the combined extracts were washed with water, dried, filtered and evaporated. The residue was purified by column chromatography (silica gel; CH$_2$Cl$_2$/CH$_3$OH(NH$_3$) 95:5). The eluent of the desired fraction was evaporated and the residue was converted into the ethanedioate (1:2) salt in ethanol. The product was filtered off and dried, yielding 0.56 parts (8.3%) of 4-amino-N-[1-[2-(1H-benzimidazol-2-ylamino)ethyl]-4-piperidinyl]-5-chloro-2,3-dihydro-2,2-dimethyl-7-benzofurancarboxamide ethanedioate(1:2) hemihydrate; mp. 211.7° C. (comp. 70).

Example 16

A mixture of 3.1 parts of 2-chloro-3-methylpyrazine, 4.4 parts of compound 14 and 0.79 parts of calciumoxide was stirred for 24 hours at 120° C. After cooling, the reaction mixture was partitioned between dichloromethane and NH$_4$OH (dil.). The aqueous layer was separated and re-extracted with dichloromethane. The combined organic layers were dried, filtered and evaporated. The residue was purified by column chromatography (silica gel; CH$_2$Cl$_2$/CH$_3$OH(NH$_3$) 98:2). The eluent of the desired fraction was evaporated and the residue was triturated in 2,2′-oxybispropane. The product was filtered off and dried, yielding 3.3 parts (59.9%) of 4-amino-5-chloro-2,3-dihydro-2,2-dimethyl-N-[1-[2-[(3-methyl-2-pyrazinyl)amino]ethyl]-4-piperidinyl]-7-benzofurancarboxamide; mp. 163.2° C. (comp. 15).

Example 17

Through a solution of 3.5 parts of intermediate 11 in 19.8 parts of ethanol and 25 parts of water was bubbled oxirane for 1 hour at room temperature. The reaction mixture was evaporated and the residue was purified by column chromatography (silica gel; CH$_2$Cl$_2$/CH$_3$OH(NH$_3$) 95:5). The eluent of the desired fraction was evaporated and the residue was crystallized from acetonitrile. The product was filtered off and dried in vacuo at 70° C., yielding 1.64 parts (40.2%) of 4-amino-5-chloro-2,3-dihydro-N-[1-(2-hydroxyethyl)-4-piperidinyl]-7-benzofurancarboxamide; mp. 185.7° C. (comp. 49).

Example 18

To a mixture of 12.2 parts of compound 8 and 83 parts of water there were added 1.53 parts of sulfuric acid. After stirring for 4½ hours at room temperature, the reaction mixture was poured into a mixture of NH$_4$OH (dil.) and ice. The product was extracted with dichloromethane and the extract was dried, filtered and evaporated. The residue was purified by column chromatography (silica gel; CH$_2$Cl$_2$/CH$_3$OH(NH$_3$) 97:3). The eluent of the desired fraction was evaporated and the residue was triturated in 2,2′-oxybispropane. The product was filtered off and dried, yielding 2.3 parts (40.3%) of 4-amino-5-chloro-2,3-dihydro-2,2-dimethyl-N-[1-(4-oxopentyl)-4-piperidinyl]-7-benzofurancarboxamide; mp. 119.2° C. (comp. 9).

Example 19 a) A mixture of 7.6 parts of compound 3; 5 parts of potassium acetate and 158 parts of methanol was hydrogenated at normal pressure and 50° C. with 2 parts of palladium-on-charcoal catalyst 10%. After the calculated amount of hydrogen was taken up, the catalyst was filtered off and the filtrate was evaporated, yielding 6.91 parts (100%) of 4-amino-2,3-dihydro-N-[1-[(tetrahydro-2-furanyl)methyl]-4-piperidinyl]-7-benzofurancarboxamide (comp. 75).

b) A mixture of 8 parts of compound 75; 5 parts of 2-iodopropane, 3.1 parts of N,N-diethylethanamine and 25.8 parts of hexamethylphosphoric triamide was stirred for 20 hours at 130° C. After cooling, the reaction mixture was poured into water. The product was extracted with dichloromethane and the extract was washed with water, dried, filtered and evaporated. The residue was taken up in 2,2′-oxybispropane. After filtration, this solution was evaporated and the residue was taken up in 2-propanol. 2,2′-Oxybispropane was added to enhance crystallization. The precipitate was filtered off and dissolved in dichloromethane. This solution was washed with water, dried, filtered and evaporated. The residue was purified by column chromatography (silica gel; $CH_2Cl_2/CH_3OH(NH_3)$ 97:3). The eluent of the desired fraction was evaporated and the residue was converted into the ethanedioate (1:1) salt. The product was filtered off and dried in vacuo at 60° C., yielding 0.3 parts (2.7%) of 2,3-dihydro-4-[(1-methylethyl)amino]-N-[1-[(tetrahydro-2-furanyl)methyl]-4-piperidinyl]-7benzofurancarboxamide ethanedioate(1:1); mp. 211.7° C. (comp. 76).

Example 20

A mixture of 5 parts of compound 63 and 230 ml of HCl 3N was stirred for 1 hour at reflux temperature. After cooling, the reaction mixture was evaporated. The residue was stirred in 5 parts of water. The product was filtered off, washed with a little water and dried in vacuo at 70° C., yielding 1.7 parts (31.5%) of 4-[[(5-amino-6-chloro-3,4-dihydro-2H-1-benzopyran-8-yl)carbonyl]amino]-1-piperidinebutanoic acid monohydrochloride monohydrate; mp. 204.5° C. (comp. 68).

All compounds listed in Table 2 were prepared following methods of preparation described in examples 7–20, as is indicated in the column Ex. No.

TABLE 2

| Co. No. | Ex. No. | L | $R^1$ | $R^2$ | —O—A— | Physical data (mp.) |
|---|---|---|---|---|---|---|
| 1 | 7 | tetrahydrofuranyl-$CH_2$— | Cl | $NH_2$ | —O—$(CH_2)_3$— | 121.0° C. |
| 2 | 8 | thiazolo-pyrimidinone-$(CH_2)_2$— ($CH_3$) | Cl | $NH_2$ | —O—$(CH_2)_3$— | 211.8° C. |
| 3 | 7 | tetrahydrofuranyl-$CH_2$— | Cl | $NH_2$ | —O—$(CH_2)_2$— | 175.4° C. |
| 4 | 10 | $CH_3$-dioxolanyl-$(CH_2)_3$— | Cl | $NH_2$ | —O—$(CH_2)_2$— | 139.8° C. |
| 5 | 18 | $CH_3$—C(O)—$(CH_2)_3$— | Cl | $NH_2$ | —O—$(CH_2)_2$— | 137.4° C. |
| 6 | 10 | $CH_3$-dioxolanyl-$(CH_2)_3$— | Cl | $NH_2$ | —O—$(CH_2)_3$— | 111.2° C. |
| 7 | 18 | $CH_3$—C(O)—$(CH_2)_3$— | Cl | $NH_2$ | —O—$(CH_2)_3$— | 104.9° C./$H_2O$ |
| 8 | 10 | $CH_3$-dioxolanyl-$(CH_2)_3$— | Cl | $NH_2$ | —O—$C(CH_3)_2$—$CH_2$— | 136.5° C. |
| 9 | 18 | $CH_3$—C(O)—$(CH_2)_3$— | Cl | $NH_2$ | —O—$C(CH_3)_2$—$CH_2$— | 119.2° C. |
| 10 | 9 | NC—$CH_2$— | Cl | $NH_2$ | —O—$(CH_2)_3$— | 194° C. |
| 11 | 12 | $H_2N$—$(CH_2)_2$— | Cl | $NH_2$ | —O—$(CH_2)_3$— | 130° C. |

TABLE 2-continued

Structure: L—N(piperidine)—NH—C(=O)—Ar where Ar is a benzene ring with R¹, R², and an —O—A— bridge

| Co. No. | Ex. No. | L | R¹ | R² | —O—A— | Physical data (mp.) |
|---|---|---|---|---|---|---|
| 12 | 16 | 3-methyl-2-(pyrazinyl)-NH—(CH₂)₂— | Cl | NH₂ | —O—(CH₂)₃— | 178.8° C. |
| 13 | 9 | NC—CH₂— | Cl | NH₂ | —O—C(CH₃)₂—CH₂— | 110° C. |
| 14 | 12 | H₂N—(CH₂)₂— | Cl | NH₂ | —O—C(CH₃)₂—CH₂— | 155° C. |
| 15 | 16 | 3-methyl-2-(pyrazinyl)-NH—(CH₂)₂— | Cl | NH₂ | —O—C(CH₃)₂—CH₂— | 163.2° C. |
| 16 | 14 | H₅C₂O—C(=O)—NH—(CH₂)₂— | Cl | NH₂ | —O—(CH₂)₃— | 160.3° C. |
| 17 | 10 | 4-F-C₆H₄—O—(CH₂)₃— | Cl | NH₂ | —O—C(CH₃)₂—CH₂— | 131.0° C. |
| 18 | 14 | H₅C₂O—C(=O)—NH—(CH₂)₂— | Cl | NH₂ | —O—C(CH₃)₂—CH₂— | 209.9° C. |
| 19 | 10 | 4-F-C₆H₄—O—(CH₂)₃— | Cl | NH₂ | —O—(CH₂)₃— | 143.1° C. |
| 20 | 7 | 1-ethyl-3-[(CH₂)₃—]benzimidazol-2(3H)-one | Cl | NH₂ | —O—C(CH₃)₂—CH₂— | 199.9° C. |
| 21 | 7 | 1-ethyl-3-[(CH₂)₃—]benzimidazol-2(3H)-one | Cl | NH₂ | —O—(CH₂)₃— | 193.8° C./(COOH)₂ ½H₂O |
| 22 | 7 | (tetrahydrofuran-2-yl)-CH₂— | Cl | NH₂ | —O—(CH₂)₂— | 190.2° C./(−) − (R) [α]$_D^{20}$$_{0.5\%CH2OH}$ = −11.7° |
| 23 | 7 | (tetrahydrofuran-2-yl)-CH₂— | Cl | NH₂ | —O—(CH₂)₂— | 191.6° C./(+) − (S) [α]$_D^{20}$$_{0.5\%CH3OH}$ = −13.1° |

TABLE 2-continued

Structure: L—N(piperidine)—4-yl—NH—C(=O)—benzene with R¹, R², and —O—A— fused ring

| Co. No. | Ex. No. | L | R¹ | R² | —O—A— | Physical data (mp.) |
|---|---|---|---|---|---|---|
| 24 | 7 | (tetrahydrofuran-2-yl)—CH₂— | Cl | NH₂ | —O—C(CH₃)₂—(CH₂)₂— | 175.7° C. |
| 25 | 11 | NC—(CH₂)₂— | Cl | NH₂ | —O—C(CH₃)₂—(CH₂)₂— | 155° C. |
| 26 | 12 | H₂N—(CH₂)₃— | Cl | NH₂ | —O—C(CH₃)₂—(CH₂)₂— | 182.8° C. |
| 27 | 9 | NC—CH₂— | Cl | NH₂ | —O—(CH₂)₂— | 227.8° C. |
| 28 | 8 | 3-methyl-2-thia-4,7-diaza-bicyclic-(CH₂)₂— | Cl | NH₂ | —O—C(CH₃)₂—(CH₂)₂— | 222° C. |
| 29 | 11 | NC—(CH₂)₂— | Cl | NH₂ | —O—(CH₂)₂— | 203.5° C. |
| 30 | 7 | 1-ethyl-3-(propyl)-benzimidazol-2-one, H₅C₂—N,N—(CH₂)₃— | Cl | NH₂ | —O—(CH₂)₂— | 149.8° C. |
| 31 | 12 | H₂N—(CH₂)₂— | Cl | NH₂ | —O—(CH₂)₂— | 157.8° C. |
| 32 | 16 | 3-methyl-2-(pyrazinylamino)—(CH₂)₂— | Cl | NH₂ | —O—(CH₂)₂— | 152.5° C./½H₂O |
| 33 | 9 | 5,6,7-trimethoxy-4-oxo-1,2,3-benzotriazin-3-yl—(CH₂)₃— | Cl | NH₂ | —O—C(CH₃)₂—CH₂— | 205.5° C. |
| 34 | 11 | NC—(CH₂)₂— | Cl | NH₂ | —O—C(CH₃)₂—CH₂— | — |
| 35 | 12 | H₂N—(CH₂)₃— | Cl | NH₂ | —O—C(CH₃)₂—CH₂— | 132.9° C./H₂O |
| 36 | 10 | (4-F—C₆H₄)₂—CH—(CH₂)₄— | Cl | H | —O—C(CH₃)₂—CH₂— | 195.0° C./HCl |
| 37 | 10 | (4-F—C₆H₄)₂—CH—(CH₂)₃— | Cl | H | —O—C(CH₃)₂—CH₂— | 133.3° C. |
| 38 | 14 | H₅C₂O—C(=O)—NH—(CH₂)₂— | Cl | NH₂ | —O—(CH₂)₂— | 166.1° C. |
| 39 | 9 | NC—(CH₂)₃— | Cl | NH₂ | —O—C(CH₃)₂—CH₂— | 165.1° C. |
| 40 | 12 | H₂N—(CH₂)₄— | Cl | NH₂ | —O—C(CH₃)₂—CH₂— | 150.7° C. |
| 41 | 12 | H₂N—(CH₂)₃— | Cl | NH₂ | —O—(CH₂)₂— | — |
| 42 | 8 | 1-ethyl-3-(butyl)-benzimidazol-2-one, H₅C₂—N,N—(CH₂)₄— | Cl | NH₂ | —O—(CH₂)₂— | 148.7° C. |

TABLE 2-continued

![Structure: L-N-piperidine-NH-C(=O)-benzene with R1, R2 substituents and -O-A- bridge]

| Co. No. | Ex. No. | L | R¹ | R² | —O—A— | Physical data (mp.) |
|---|---|---|---|---|---|---|
| 43 | 8 | H₅C₂—N(C(=O))N—(CH₂)₄— fused to benzene (benzimidazolinone) | Cl | NH₂ | —O—(CH₂)₃— | 155.6° C./HCl 3/2H₂O |
| 44 | 8 | H₅C₂—N(C(=O))N—(CH₂)₃— (imidazolidinone) | Cl | NH₂ | —O—(CH₂)₂— | 182.0° C. |
| 45 | 9 | 3-(indol-3-yl)—(CH₂)₂— | Cl | NH₂ | —O—C(CH₃)₂—CH₂— | 209.0° C. |
| 46 | 10 | H₅C₂O—C(=O)—NH—(CH₂)₂— | Cl | H | —O—C(CH₃)₂—CH₂— | 229.0° C./HCl |
| 47 | 9 | 3,4,5-(CH₃O)₃—C₆H₂—C(=O)—(CH₂)₃— | Cl | NH₂ | —O—(CH₂)₂— | 202.1° C./(COOH)₂ |
| 48 | 7 | H₅C₂—N(C(=O))N—(CH₂)₃— (imidazolidinone) | Cl | NH₂ | —O—(CH₂)₃— | 192.9° C./(COOH)₂ H₂O |
| 49 | 17 | HO—(CH₂)₂— | Cl | NH₂ | —O—(CH₂)₂— | 185.7° C. |
| 50 | 9 | (CH₃)₂CH—O—(CH₂)₂— | Cl | NH₂ | —O—(CH₂)₃— | 197.9° C./(COOH)₂ ½H₂O |
| 51 | 9 | H₂C₂O—C(=O)—CH₂— | Cl | NH₂ | —O—(CH₂)₃— | 98.8° C. |
| 52 | 9 | piperidin-1-yl—(CH₂)₂— | Cl | NH₂ | —O—(CH₂)₃— | 250.5° C./2HCl ½H₂O |
| 53 | 10 | (4-F—C₆H₄)₂—CH—(CH₂)₄— | Cl | NH₂ | —O—C(CH₃)₂—CH₂— | 169.1° C. |
| 54 | 10 | (4-F—C₆H₄)₂—CH—(CH₂)₃— | Cl | NH₂ | —O—C(CH₃)₂—CH₂— | 169.0° C. |
| 55 | 10 | H₅C₂O—C(=O)—NH—(CH₂)₃— | Cl | H | —O—C(CH₃)₂—CH₂— | 156.5° C./HCl H₂O |
| 56 | 10 | (CH₃)₂CH—O—(CH₂)₂— | Cl | NH₂ | —O—(CH₂)₂— | 237.2° C./HCl |

TABLE 2-continued

| Co. No. | Ex. No. | L | R¹ | R² | —O—A— | Physical data (mp.) |
|---|---|---|---|---|---|---|
| 57 | 10 | piperidinyl-N—(CH$_2$)$_2$— | Cl | NH$_2$ | —O—(CH$_2$)$_2$— | 193.0° C. |
| 58 | 9 | H$_5$C$_2$O—C(=O)—CH$_2$— | Cl | NH$_2$ | —O—(CH$_2$)$_2$— | 135.2° C. |
| 59 | 20 | HO—C(=O)—CH$_2$— | Cl | NH$_2$ | —O—(CH$_2$)$_2$— | 273.5° C./HCl ½H$_2$O |
| 60 | 20 | HO—C(=O)—CH$_2$— | Cl | NH$_2$ | —O—(CH$_2$)$_3$— | 253.8° C./H$_2$O |
| 61 | 7 | tetrahydrofuran-2-yl—CH$_2$— | Cl | NH$_2$ | —O—C(CH$_3$)$_2$—CH$_2$— | 147.6° C. |
| 62 | 10 | H$_5$C$_2$O—C(=O)—(CH$_2$)$_3$— | Cl | NH$_2$ | —O—(CH$_2$)$_2$— | 220.7° C./HCl |
| 63 | 10 | H$_5$C$_2$O—C(=O)—(CH$_2$)$_3$— | Cl | NH$_2$ | —O—(CH$_2$)$_3$— | 186.4° C./(COOH)$_2$ |
| 64 | 9 | 4-F-C$_6$H$_4$—CH=CH—(CH$_2$)$_2$— | Cl | NH$_2$ | —O—C(CH$_3$)$_2$—CH$_2$— | 128.1° C./(E) |
| 65 | 8 | 6-methyl-3-oxo-2,3-dihydropyridazin-2-yl—(CH$_2$)$_2$— | Cl | NH$_2$ | —O—(CH$_2$)$_2$— | 181.1° C. |
| 66 | 8 | 6-methyl-3-oxo-2,3-dihydropyridazin-2-yl—(CH$_2$)$_2$— | Cl | NH$_2$ | —O—(CH$_2$)$_3$— | 90.3° C. |
| 67 | 20 | HO—C(=O)—(CH$_2$)$_3$— | Cl | NH$_2$ | —O—(CH$_2$)$_2$— | 260.3° C./HCl ½H$_2$O |
| 68 | 20 | HO—C(=O)—(CH$_2$)$_3$— | Cl | NH$_2$ | —O—(CH$_2$)$_3$— | 204.5° C./HCl H$_2$O |
| 69 | 10 | 4-F-C$_6$H$_4$—CH=CH—(CH$_2$)$_2$— | Cl | H | —O—C(CH$_3$)$_2$—CH$_2$— | 208.9° C./HCl 3/2H$_2$O |

TABLE 2-continued

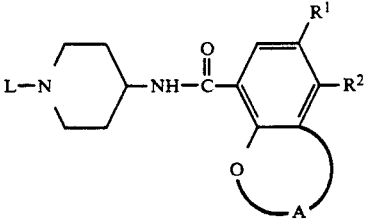

| Co. No. | Ex. No. | L | R¹ | R² | —O—A— | Physical data (mp.) |
|---|---|---|---|---|---|---|
| 70 | 15 | 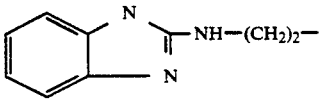 | Cl | $NH_2$ | $-O-C(CH_3)_2-CH_2-$ | 211.7° C./2(COOH)₂ ½H₂O |
| 71 | 13 | $H_2N-(CH_2)_3-$ | Cl | H | $-O-C(CH_3)_2-CH_2-$ | 123.1° C./½H₂O |
| 72 | 7 | 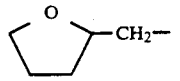 | Cl | H | $-O-C(CH_3)_2-CH_2-$ | 217.0° C./HCl ½H₂O |
| 73 | 7 | 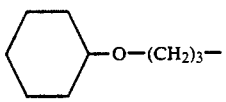 | Cl | H | $-O-C(CH_3)_2-CH_2-$ | 154.5° C./HCl H₂O |
| 74 | 7 | 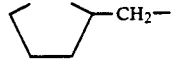 | Cl | H | $-O-(CH_2)_2-$ | 115° C. |
| 75 | 19a | 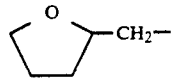 | H | $NH_2$ | $-O-(CH_2)_2-$ | — |
| 76 | 19b | 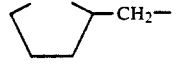 | H | * | $-O-(CH_2)_2-$ | 211.7° C./(COOH)₂ |
| 77 | 9 | 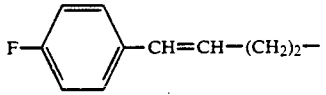 | Cl | H | $-O-(CH_2)_2-$ | 134.8° C./(E) |
| 78 | 8 | 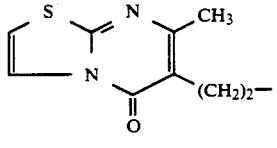 | Cl | H | $-O-C(CH_3)_2-(CH_2)_2-$ | 97.7° C. |
| 79 | 10 | 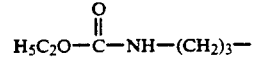 | Cl | H | $-O-C(CH_3)_2-(CH_2)_2-$ | 122.6° C. |
| 80 | 13 | $H_2N-(CH_2)_3-$ | Cl | H | $-O-C(CH_3)_2-(CH_2)_2-$ | 128.6° C. |
| 81 | 7 | 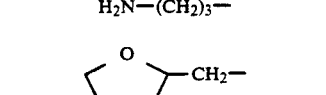 | Cl | H | $-O-C(CH_3)_2-(CH_2)_2-$ | 119.0° C. |
| 82 | 10 | $(CH_3)_2CH-O-(CH_2)_3-$ | Cl | H | $-O-C(CH_3)_2-(CH_2)_2-$ | 215.4° C./HCl |
| 83 | 9 | $NC-CH_2$ | H | * | $-O-C(CH_3)_2-CH_2-$ | — |
| 84 | 12 | $H_2N-(CH_2)_2-$ | H | * | $-O-C(CH_3)_2-CH_2-$ | — |
| 85 | 10 | 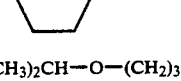 | Cl | H | $-O-C(CH_3)_2-(CH_2)_2-$ | 208.5° C./HCl |
| 86 | 13 | $H_2N-(CH_2)_2-$ | Cl | H | $-O-C(CH_3)_2-CH_2-$ | 2 HCl |
| 87 | 9 | $4-F-C_6H_4-O-(CH_2)_3-$ | Cl | H | $-O-(CH_2)_2-$ | 134.0° C. |

TABLE 2-continued

| Co. No. | Ex. No. | L | R¹ | R² | —O—A— | Physical data (mp.) |
|---|---|---|---|---|---|---|
| 88 | 10 | (4-F—C₆H₄)₂CH—(CH₂)₂— | Cl | H | —O—C(CH₃)₂—CH₂— | 193.4° C./HCl |
| 89 | 7 | H₅C₂—N(C=O)N—(CH₂)₃—[benzimidazolone] | Cl | H | —O—(CH₂)₂— | 141.5° C. |
| 90 | 7 | cyclopentyl-CH₂— | Cl | NH₂ | —O—(CH₂)₃— | 131.8° C. |
| 91 | 17 | HO—(CH₂)₂— | Cl | NH₂ | —O—(CH₂)₃— | 126.0° C. |
| 92 | 10 | (CH₃)₂CH—C(=O)—(CH₂)₃— | Cl | H | —O—(CH₂)₂— | 104.5° C. |
| 93 | 7 | H₅C₂—N(C=O)N—(CH₂)₄—[benzimidazolone] | Cl | H | —O—(CH₂)₂— | 112.8° C. |
| 94 | 9 | NC—CH₂— | Cl | H | —O—(CH₂)₂— | 208.6° C. |
| 95 | 8 | CH₃,(CH₂)₃— dioxolane | Cl | H | —O—(CH₂)₂— | 117.0° C. |
| 96 | 18 | CH₃—C(=O)—(CH₂)₃— | Cl | H | —O—(CH₂)₂— | 89.1° C. |
| 97 | 7 | tetrahydrofuryl-CH₂— | Cl | NH₂ | —O—(CH₂)₃— | 126.5° C./(−) − (R) $[\alpha]_D^{20}{}_{1\%CH_3OH} = -11.8°$ |

* = —NH—CH(CH₃)₂

The compounds listed in Table 3 are prepared according to similar procedures as described in any of the preceding examples (7-20).

TABLE 3

| Co. No. | L | —O—A— |
|---|---|---|
| 98 | 6-chloro-3-oxo-2,3-dihydropyridazin-2-yl-(CH₂)₂— | —O—(CH₂)₃— |
| 99 | 1-oxo-phthalazin-2-yl-(CH₂)₂— | —O—(CH₂)₃— |
| 100 | chroman-2-yl-CH₂— | —O—(CH₂)₃— |
| 101 | pyridin-2-yl-CH₂— | —O—(CH₂)₃— |
| 102 | 2,4-dioxo-1,2,3,4-tetrahydroquinazolin-3-yl-(CH₂)₃— | —O—(CH₂)₃— |
| 103 | (3-cyanopyridin-2-yl)NH—(CH₂)₄— | —O—(CH₂)₃— |
| 104 | (3-cyanopyridin-2-yl)NH—(CH₂)₂— | —O—(CH₂)₃— |
| 105 | 6-methyl-7-oxo-2,3-dihydro-7H-thiazolo[3,2-a]pyrimidin-5-yl-(CH₂)₂— | —O—(CH₂)₃— |
| 106 | C₆H₅N(COOC₂H₅)—(CH₂)₂— | —O—(CH₂)₃— |
| 107 | CH₃O—(CH₂)₃— | —O—(CH₂)₃— |

TABLE 3-continued

[Structure: L-N(piperidine)-NH-C(=O)-Ar, where Ar is a benzene ring with Cl, NH2, and a fused -O-A- bridge]

| Co. No. | L | —O—A— |
|---|---|---|
| 108 | [piperidine-N-C(=O)-(CH₂)₃—] | —O—(CH₂)₃— |
| 109 | (CH₃)₂CH—NH—(CH₂)₂— | —O—(CH₂)₃— |
| 110 | (CH₃)₂CH—NH—(CH₂)₄— | —O—(CH₂)₃— |
| 111 | H—C(=O)—NH—(CH₂)₄— | —O—(CH₂)₃— |
| 112 | H—C(=O)—NH—(CH₂)₂— | —O—(CH₂)₃— |
| 113 | H₅C₂O—C(=O)—NH—(CH₂)₄— | —O—(CH₂)₃— |
| 114 | H₅C₂O—C(=O)—NH—(CH₂)₂— | —O—(CH₂)₃— |
| 115 | [cyclohexyl-] | —O—(CH₂)₃— |
| 116 | HO—(CH₂)₂—O—(CH₂)₂— | —O—(CH₂)₃— |
| 117 | [benzimidazolinon-1-yl]-(CH₂)₃— | —O—C(CH₃)₂—CH₂— |
| 118 | 4-F-C₆H₄—CH₂— | —O—C(CH₃)₂—CH₂— |
| 119 | 4-F-C₆H₄—C(=O)—(CH₂)₃— | —O—C(CH₃)₂—CH₂— |
| 120 | CH₂=CH—CH₂— | —O—C(CH₃)₂—CH₂— |
| 121 | cyclopropyl-CH₂— | —O—C(CH₃)₂—CH₂— |

TABLE 3-continued

[Structure: L—N(piperidine)—NH—C(=O)—benzene ring with Cl, NH₂, and O—A substituents]

| Co. No. | L | —O—A— |
|---|---|---|
| 122 | [cyclobutyl]—CH₂— | —O—C(CH₃)₂—CH₂— |

C. PHARMACOLOGICAL EXAMPLES

The useful gastrointestinal motility stimulating properties of the compounds of the present invention and in particular their capability to enhance the contractility of the colon can be demonstrated in the following test.

Example 21

Colon ascendens induced contractions

The experiment was conducted according to similar procedures as described in The Journal of Pharmacology and Experimental Therapeutics, 234, 776–783 (1985). Colon segments, 4.5 cm long, were vertically suspended with a preload of 2 g in 100 ml of a De Jalon solution [KCl 5.6 mM; CaCl$_2$.2H$_2$O 0.54 mM; NaHCO$_3$ 5.9 mM; NaCl 154.1 mM; glucose 2.8 mM] at 37.5° C. and gassed with a mixture of 95% O$_2$ and 5% CO$_2$. Contractions were measured isotonically with a HP 7 DCDT-1000, JSID Displacement Transducer Control Unit. After a stabilization period of about 20 minutes, $3.4 \times 10^{-6}$M methacholine was given at a time interval of 15 minutes. When reproducible contractions were obtained, the test compound was administered to the bathing solution. The compound effect was followed for 10 minutes and expressed relative to the maximal concentrations induced by $3.4 \times 10^{-6}$M methacholine. The % effect for a representative number of compounds of formula (I) is depicted hereinbelow in Table 4

TABLE 4

| Co. No. | Dose $3.10^{-6}$M | Dose $3.10^{-7}$M |
|---|---|---|
| 2 | — | 28 |
| 3 | 52 | 20 |
| 16 | — | 30 |
| 17 | — | 30 |
| 19 | — | 35 |
| 20 | — | 41 |
| 22 | 46 | 29 |
| 23 | 48 | 26 |
| 30 | — | 36 |
| 65 | — | 27 |
| 81 | — | 27 |

D. COMPOSITION EXAMPLES

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

Example 22: Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example 23: Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example 24: Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90 ®) in about 200 ml of water. The wet powder mixture is sieved, dried and sieved again. Then there are added 100 g microcrystalline cellulose (Avicel ®) and 15 g hydrogenated vegetable oil (Sterotex ®). The whole is mixed well and compressed into tablets, giving 10.000 tablets, each comprising 10 mg of the active ingredient.

Coating

To a solution of 10 g methyl cellulose (Methocel 60 HG ®) in 75 ml of denaturated ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

We claim:

1. A compound of the formula:

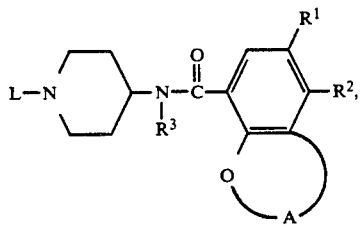
(I)

an N-oxide form, a salt or a stereochemically isomeric form thereof, wherein:

A is a radical of the formula:

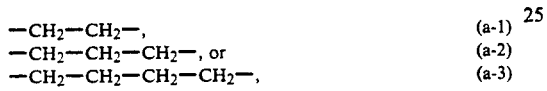

wherein one or two hydrogen atoms in said radicals (a-1) to (a-3) may be replaced by a $C_{1-6}$alkyl radical;

$R^1$ is hydrogen or halo;

$R^2$ is hydrogen, amino, mono- or di($C_{1-6}$alkyl)amino or $C_{1-6}$alkylcarbonylamino;

$R^3$ is hydrogen or $C_{1-6}$alkyl;

L is a radical of the formula:

wherein Alk is $C_{1-6}$alkanediyl; and $R^4$ is hydrogen, cyano, $C_{1-6}$alkylsulfonylamino, $C_{3-6}$cycloalkyl, $C_{5-6}$cycloalkanone, aryl or Het;

wherein:

aryl represents unsubstituted phenyl or phenyl substituted with 1, 2 or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino or aminocarbonyl; and wherein (I) Het represents a group of the formula:

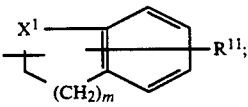

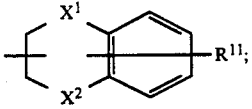

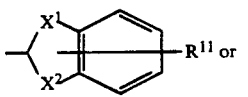

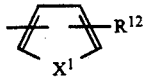

wherein:

each $X^1$ and $X^2$ independently represents O or S;

M is 1 or 2;

each $R^{11}$ represents hydrogen, $C_{1-4}$alkyl, $C_{1-4}$alkyloxy$C_{1-4}$alkyl or hydroxy$C_{1-4}$alkyl; and $R^{12}$ represents hydrogen, halo or $C_{1-4}$alkyl, or (II) Het represents a cyclic ether selected from the group consisting of 1,3-dioxolanyl optionally substituted with $C_{1-4}$alkyl; 1,3-dioxanyl optionally substituted with $C_{1-4}$alkyl; tetrahydrofuranyl optionally substituted with $C_{1-4}$alkyl; tetrahydropyranyl optionally substituted with $C_{1-4}$alkyl; 2,3-dihydro-1,4-benzodioxinyl; 2,3-dihydrobenzofuran and 3,4-dihydro-1(2H)-benzopyranyl; or (III) Het represents a member selected from the group consisting of pyrrolidinyl; piperidinyl; pyridinyl which is optionally substituted with one or two substituents each independently selected from halo, hydroxy, cyano, $C_{1-6}$alkyl, trifluoromethyl, $C_{1-6}$alkyloxy, aminocarbonyl, mono and di($C_{1-6}$alkyl)aminocarbonyl, amino, mono and di($C_{1-6}$alkyl)amino and $C_{1-6}$alkyl-oxycarbonyl; pyrimidinyl which is optionally substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl which is optionally substituted with $C_{1-6}$alkyl or halo; pyrazinyl which is optionally substituted with one or two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxy-carbonyl; pyrrolyl which is optionally substituted with $C_{1-6}$alkyl; pyrazolyl which is optionally substituted with $C_{1-6}$alkyl; imidazolyl which is optionally substituted with $C_{1-6}$alkyl; triazolyl which is optionally substituted with $C_{1-6}$alkyl; quinolinyl optionally substituted with up to two substituents each independently selected from halo, hydroxy, cyano, $C_{1-6}$alkyl, $C_{1-6}$alkyloxy, amino, mono and di($C_{1-6}$alkyl)amino and trifluoromethyl; isoquinolinyl optionally substituted with up to two substituents each independently selected from halo, hydroxy, cyano, $C_{1-6}$alkyl, $C_{1-6}$alkyloxy, amino, mono and di($C_{1-6}$alkyl)amino and trifluoromethyl; quinoxalinyl optionally substituted with up to two substituents each independently selected from $C_{1-6}$alkyl, hydroxy, halo, cyano and $C_{1-6}$alkyloxy; quinazolinyl optionally substituted with $C_{1-6}$alkyl; benzimidazolyl optionally substituted with $C_{1-6}$alkyl; indolyl optionally substituted with $C_{1-6}$alkyl; 5,6,7,8-tetrahydroquinolinyl optionally substituted with up to two substituents each independently selected from halo, hydroxy, cyano, $C_{1-6}$alkyl, $C_{1-6}$alkyloxy, amino, mono- and di($C_{1-6}$alkyl)amino and trifluoromethyl; 5,6,7,8-tetrahydroquinoxalinyl optionally substituted with up to two substituents each independently selected from $C_{1-6}$alkyl, hydroxy, halo, cyano and $C_{1-6}$alkyloxy; thiazolyl optionally substituted with $C_{1-6}$alkyl; oxazolyl optionally substituted with $C_{1-6}$alkyl; benzoxazolyl optionally substituted with $C_{1-6}$alkyl; and benzothiazolyl optionally substituted with $C_{1-6}$alkyl; or (IV) Het represents a group of the formula:

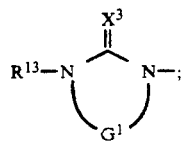 (4-1)

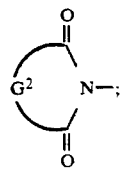 (d-2)

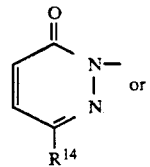 (d-3) or

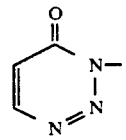 (d-4)

$X^3$ is O or S;
$R^{13}$ is hydrogen, $C_{1-6}$alkyl or aryl$C_{1-6}$alkyl;
$R^{14}$ is hydrogen, halo, $C_{1-6}$alkyl or aryl;
$G^1$ is —CH$_2$—CH$_2$—, —CH=CH—, —N=N—, —C(=O)—CH$_2$— or —CH$_2$—CH$_2$—CH$_2$—, wherein one or two hydrogen atoms each independently may be replaced by $C_{1-6}$alkyl; and
$G^2$ is —CH$_2$—CH$_2$—, —CH$_2$—N(R$^{13}$)— or —CH$_2$—CH$_2$—CH$_2$—, wherein one or two hydrogen atoms each independently may be replaced by $C_{1-6}$alkyl; or (V) Het represents a group of the formula:

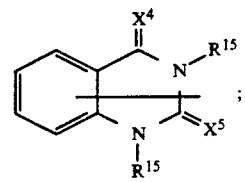 (d-5)

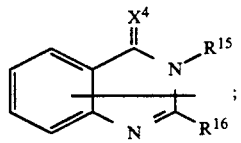 (d-6)

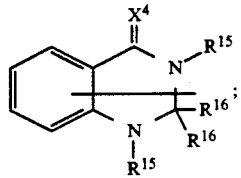 (d-7)

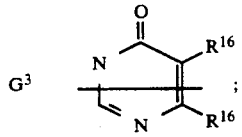 (d-8)

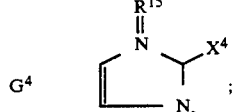 (d-9)

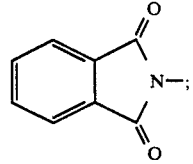 (d-10)

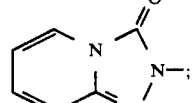 (d-11)

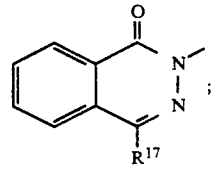 (d-12)

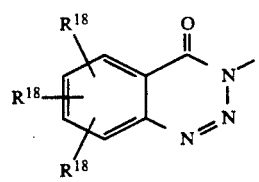 (d-13)

wherein $X^4$ and $X^5$ each independently are O or S;
each $R^{15}$ independently is hydrogen, $C_{1-6}$alkyl or aryl$C_{1-6}$alkyl;
each $R^{16}$ independently is hydrogen, halo, $C_{1-6}$alkyl or $C_{1-6}$alkyloxy;
$R^{17}$ is hydrogen, halo, $C_{1-6}$alkyl or aryl; and
each $R^{18}$ independently is hydrogen, $C_{1-6}$alkyloxy or $C_{1-6}$alkyl,
$G^3$ is —CH=CH—CH=CH—, —(CH$_2$)$_4$—, —S—(CH$_2$)$_2$—, —S—(CH$_2$)$_3$—, —S—CH=CH—, —CH=CH—O—, —NH—(CH$_2$)$_2$—, —NH—(CH$_2$)$_3$—, —NH—CH=CH—, —NH—N=

CH—CH$_2$—, —NH—CH=N— or —NH—N=CH—; and

G$^4$ is —CH=CH—CH=CH—, —CH=CCl—CH=CH—, —CCl=CH—CH=CH—, —N=CH—CH=CH—, —CH=N—CH=CH—, —CH=CH—N=CH—, —CH=CH—CH=N—, —N=CH—N=CH— or —CH=N—CH=N—, wherein the radicals (d-5), (d-6), (d-7) and (d-8) may be connected to Alk by replacing either a hydrogen or a radical R$^{15}$ or R$^{16}$ by a free bond.

2. A compound according to claim 1 wherein Het is selected from the group consisting of piperidinyl; pyridinyl optionally substituted with up to two substituents selected from C$_{1-4}$alkyl, cyano, halo and trifluoromethyl; pyrazinyl optionally substituted with cyano, halo, C$_{1-4}$alkyloxycarbonyl and C$_{1-4}$alkyl; and pyridazinyl optionally substituted with halo.

3. A compound according to claim 1 wherein Het is selected from the group consisting of 2,3-dihydro-2-oxo-1H-benzimidazolyl optionally substituted with C$_{1-6}$alkyl; 2-oxo-1-imidazolidinyl optionally substituted with C$_{1-4}$alkyl; 2,5-dioxo-1-imidazolidinyl optionally substituted with C$_{1-4}$alkyl; 3,4-dihydro-4-oxo-1,2,3-benzotriazin-3-yl optionally substituted with 1, 2 or 3 C$_{1-4}$alkyloxy groups; 1-oxo-2(1H)-phthalazinyl; 2,3-dihydro-5-oxo-5H-thiazolo[3,2-a]pyrimidin-6-yl optionally substituted with C$_{1-4}$alkyl; 5-oxo-5H-thiazolo[3,2-a]pyrimidin-6-yl optionally substituted with C$_{1-4}$alkyl; 1,6-dihydro-6-oxo-1-pyridazinyl optionally substituted with C$_{1-4}$alkyl or halo; and 1,2,3,4-tetrahydro-2,4-dioxo-3-quinazolinyl.

4. A compound according to claim 1 wherein R$^1$ is hydrogen or halo; R$^2$ is hydrogen, amino or C$_{1-6}$alkylamino; and R$^3$ is hydrogen.

5. A compound according to claim 1 wherein A is a radical of formula (a-1) or (a-2) wherein the carbon atom adjacent to the oxygen atom is optionally substituted with one or two C$_{1-4}$alkyl substituents.

6. A compound according to claim 5 wherein

Het is pyrrolidinyl; piperidinyl; pyridinyl optionally substituted with C$_{1-6}$alkyl or cyano; pyrazinyl optionally substituted with C$_{1-6}$alkyl; benzimidazolyl optionally substituted with C$_{1-6}$alkyl; or indolyl optionally substituted with C$_{1-6}$alkyl; or Het is a radical of formula (c-1), (c-2) or (c-4); or Het is a radical of formula (d-1), (d-3), (d-5), (d-8), (d-9), (d-12) or (d-13).

7. A compound according to claim 6 wherein Het is tetrahydrofuranyl optionally substituted with C$_{1-4}$alkyl; 1,3-dioxolanyl optionally substituted with C$_{1-4}$alkyl; 3,4-dihydro-1(2H)-benzopyranyl; pyrrolidinyl; piperidinyl; pyridinyl optionally substituted with cyano; pyrazinyl optionally substituted with C$_{1-4}$alkyl; benzimidazolyl; indolyl; 2,3-dihydro-2-oxo-1H-benzimidazolyl optionally substituted with C$_{1-4}$alkyl; 2-oxo-1-imidazolidinyl optionally substituted with C$_{1-4}$alkyl; 3,4-dihydro-4-oxo-1,2,3-benzotriazin-3-yl optionally substituted with three C$_{1-4}$alkyloxy groups; 1-oxo-2(1H)-phthalazinyl; 2,3-dihydro-5-oxo-5H-thiazolo-[3,2-a]pyrimidin-6-yl optionally substituted with C$_{1-4}$alkyl; 5-oxo-5H-thiazolo-[3,2-a]pyrimidin-6-yl optionally substituted with C$_{1-4}$alkyl; 1,6-dihydro-6-oxo-1-pyridazinyl optionally substituted with C$_{1-4}$alkyl or halo; and 1,2,3,4-tetrahydro-2,4-dioxo-3-quinazolinyl.

8. A compound according to claim 4 wherein R$^4$ is hydrogen, cyano, C$_{3-6}$cycloalkyl, C$_{5-6}$cycloalkanone, aryl, or Het.

9. A compound according to claim 8 wherein Alk is C$_{1-4}$alkanediyl and R$^4$ is cyano, C$_{3-6}$cycloalkyl, or Het.

10. A compound according to claim 6 wherein R$^1$ is hydrogen or chloro; R$^2$ is hydrogen, amino, or (1-methylethyl)amino; R$^3$ is hydrogen; and R$^4$ is cyano, cyclopentyl, tetrahydrofuranyl, piperidinyl, 7-methyl-5-oxo-5H-thiazolo[3,2-a]pyrimidin-6-yl, 3-ethyl-2,3-dihydro-2-oxo-1H-benzimidazolyl, or 1,6-dihydro-3-methyl-6-oxo-1-pyridazinyl.

11. A compound according to claim 1 wherein said compound is a member selected from the group consisting of:

5-amino-6-chloro-3,4-dihydro-N-[1-[2-(7-methyl-5-oxo-5H-thiazolo[3,2-a]pyrimidin-6-yl)ethyl]-4-piperidinyl]-2H-1-benzopyran-8-carboxamide;

4-amino-5-chloro-2,3-dihydro-N-[1-[(tetrahydro-2-furanyl)methyl]-4-piperidinyl]-7-benzofurancarboxamide;

(−)-(R)-4-amino-5-chloro-2,3-dihydro-N-[1-[(tetrahydro-2-furanyl)methyl]-4-piperidinyl-7-benzofurancarboxamide;

(+)-(S)-4-amino-5-chloro-2,3-dihydro-N-[1-[(tetrahydro-2-furanyl)methyl]-4-piperidinyl-7-benzofurancarboxamide;

5-amino-6-chloro-3,4-dihydro-N-[1-[(tetrahydro-2-furanyl)methyl]-4-piperidinyl]-2H-1-benzopyran-8-carboxamide;

(−)-(R)-5-amino-6-chloro-3,4-dihydro-N-[1-[(tetrahydro-2-furanyl)methyl]-4-piperidinyl]-2H-1-benzopyran-8-carboxamide;

5-amino-6-chloro-N-[1-[4-(3-ethyl-2,3-dihydro-2-oxo-1H-benzimidazol-1-yl)butyl]-4-piperidinyl]-3,4-dihydro-2H-1-benzopyran-8-carboxamide;

or a stereochemically isomeric form or a pharmaceutically acceptable acid addition salt thereof.

12. A pharmaceutical composition comprising an inert carrier and as active ingredient a gastrointestinal motility stimulating amount of a compound as claimed in any of claims 1–11.

13. A method of treating warm-blooded animals suffering from a decreased peristalsis of the gastrointestinal system, which method comprises the systemic administration to said warm-blooded animals of an effective gastrointestinal stimulating amount of a compound as claimed in any of claims 1–11.

* * * * *

UNITED STATES PATENT AND TRADEMARK OFFICE
CERTIFICATE OF CORRECTION

PATENT NO. : 5,185,335
DATED : February 9, 1993
INVENTOR(S) : Georges H. P. Van Daele et al It is certified that error appears in the above-indentified patent and that said Letters Patent is hereby corrected as shown below:

In Col. 58, between lines 16 and 27, formulas (d-8) and (d-9) should appear as follows:

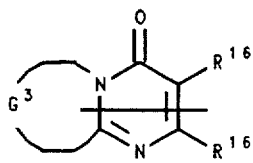

(d-8)

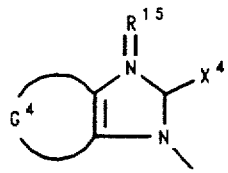

(d-9)

Signed and Sealed this

Eleventh Day of January, 1994

Attest:

BRUCE LEHMAN

*Attesting Officer*  *Commissioner of Patents and Trademarks*